(12) United States Patent
Michael et al.

(10) Patent No.: US 6,316,600 B1
(45) Date of Patent: Nov. 13, 2001

(54) METHODS FOR THE PRODUCTION OF CHICKEN MONOCLONAL ANTIBODIES

(75) Inventors: Nancy M. Michael, Chicago, IL (US); Mary Ann V Accavitti, Pelham, AL (US); Craig B. Thompson, Chicago, IL (US)

(73) Assignee: Arch Development Corporation, Chicago, IL (US)

( * ) Notice: Subject to any disclaimer, the term of this patent is extended or adjusted under 35 U.S.C. 154(b) by 0 days.

(21) Appl. No.: 08/907,146

(22) Filed: Aug. 6, 1997

Related U.S. Application Data

(63) Continuation of application No. 08/751,359, filed on Nov. 18, 1996.

(51) Int. Cl.[7] .................. C07K 16/00; A61K 39/395; C12P 21/04; C12N 5/06
(52) U.S. Cl. .................. 530/388.1; 424/133.1; 424/136.1; 424/141.1; 435/70.21; 435/326; 435/328; 435/344.1; 530/387.3; 530/388.1
(58) Field of Search ............. 424/133.1, 176.1, 424/141.1; 435/172.2, 70.21, 172.3, 328, 326, 344.1; 530/387.3, 388.1; 935/15

(56) References Cited

U.S. PATENT DOCUMENTS

| | | | |
|---|---|---|---|
| 5,028,540 | 7/1991 | Humphries | 435/240.2 |
| 5,049,502 | 9/1991 | Humphries | 435/240.2 |
| 5,411,881 | 5/1995 | Matsuda et al. | 435/240.27 |
| 5,449,610 | 9/1995 | Lillehoj | 435/7.24 |

OTHER PUBLICATIONS

Alonso et al., "Analysis of the Expression of Murine λ Genes Transfected into Immunocompetent Cell Lines", *Molecular Immunology*, vol. 27:2, 115–127, 1990.

Baba et al., "Cell Lines Derived from Avian Lymphomas Exhibit Two Distinct Phenotypes", *Virology*, 144, 139–151, 1985.

Bauwens et al., "Production, Purification and Characterization of Antibodies to 1,25–dihydroxyvitamin D Raised in Chicken Egg Yolk", *Clinica Chimica Acta*, 170, 37–44, 1987.

Bothwell et al., "Heavy Chain Variable Region Contribution to the $Np^b$ Family of Antibodies: Somatic Mutation Evident in a γ2a Variable Region", *Cell*, vol. 24, 625–637, 1981.

Buerstedde et al., "Light Chain Gene Conversion Continues at High Rate in an ALV–Induced Cell Line", *The EMBO Journal*, 9:3, 921–927, 1990.

Burger et al., "Antibodies to Human Plasma Kallikrein From Egg Yolks of an Immunized Hen: Preparation and Characterization", *Thrombosis Research*, 40, 283–288, 1985.

Carroll and Stollar, Ántibodies to Calf Thymus RNA Polymerase II from Egg Yolks of Immunized Hens, *The Journal of Biological Chemistry*, vol. 258:1, 24–26, 1983.

Cinader, "Specificity and Inheritance of Antibody Response: A Possible Steering Mechanism", *Nature*, 188, 619–622, 1960.

Coloma et al., "Novel Vectors for the Expression of Antibody Molecules Using Variable Regions Generated by Polymerase Chain Reaction", *Journal of Immunological Methods*, 152, 89–104, 1992.

(List continued on next page.)

*Primary Examiner*—Rodney P. Swartz
(74) *Attorney, Agent, or Firm*—Fulbright & Jaworski LLP

(57) ABSTRACT

The present invention provides methods for producing antibodies against a variety of antigens, including mammalian antigens with highly conserved epitopes. In addition, the present invention provides improved methods and compositions for the cloning and manipulation of immunoglobulin genes as well as antibodies derived therefrom.

17 Claims, 6 Drawing Sheets

(1 of 6 Drawing Sheet(s) Filed in Color)

OTHER PUBLICATIONS

Denning, et al., "Localization of Cystic Fibrosis Transmembrane Conductance Regulator in Chloride Secretory Epithelia", *J. Clin. Invest.,* vol. 89, 339–349, 1992.

Diamond et al., "A Cross–species Analysis of the Cystic Fibrosis Transmembrane Conductance Regulator", *The Journal of Biological Chemistry,* vol. 266:33, 22761–22769, 1991.

Fertel et al., "Formation of Antibodies to Prostaglandins in the Yolk of Chicken Eggs", *Biochemical and Biophysical Research Communications,* vol. 102:3, 1028–1033, 1981.

Gregory et al., "Expression and Characterization of the Cystic Fibrosis Transmembrane Conductance Regulator", *Nature,* 347, 382–386, 1990.

Hadge and Ambrosius, Évolution of Low Molecular Weight Immunoglobulins—IV. IgY–Like Immunoglobulins of Birds, Reptiles and Amphibians, Precursors of Mammalian IgA, *Molecular Immunology,* vol. 21:8, 699–707, 1984.

Heinrichs et al., "Universal Cloning and Direct Sequencing of Rearranged Antibody V Genes Using C Region Primers, Biotin–Captured cDNA and One–Side PCR", *Journal of Immunological Methods,* 178, 241–251, 1995.

Honjo et al., "Cloning and Complete Nucelotide Sequence of Mouse Immunoglobulin γ1 Chain Gene", *Cell,* vol. 18, 559–568, 1979.

Horton et al., "Exploitation of Phylogenetic Distance in Cell Surface Immune Labeling: Studies with Beta$_2$–Microglobulin", *The Journal of Investigative Dermatology,* 85, 96–99, 1984.

Huston et al., "Protein Engineering of Antibody Binding Sites: Recovery of Specific Activity in an Anti–Digoxin Single–Chain Fv Analogue Produced in *Escherichia coli*", *Proc. Nat'l. Acad. Sci. USA,* vol. 85, 5879–5883, 1988.

Kim et al., "Ongoing Diversification of the Rearranged Immunoglobulin Light–Chain Gene in a Bursal Lymphomas Cell Line", *Molecular and Cellular Biology,* 10:6, 1990.

Kohler and Milstein,"Derivation of Specific Antibody–Producing Tissue Culture and Tumor Lines by Cell Fusion", *Eur.J. Immunol.,* 6, 511–519, 1976.

Kohler and Milstein, "Continuous Cultures of Fused Cells Secreting Antibody of Predefined Specificity", *Nature,* vol. 256, 495–497, 1975.

Larrick et al., "Rapid Cloning of Rearranged Immunoglobulin Genes from Human Hybridoma Cells Using Mixed Primers and the Ppolymerse Chain Reaction", *Biochemical and Biophysical Research Communications,* vol. 160:3, 1250–1256, 1989.

Larsson et al., "Chicken Antibodies: Taking Advantage of Evolution—A Review", *Review,* 1807–1812, 1993.

Lee et al., "Production and Characterization of Anti–Human Insulin Antibodies in the Hen's Egg", *Agric. Biol. Chem.,* 55:8, 2141–2143, 1991.

Macejak and Sarnow, "Internal Initiation of Tranlation Mediated by the 5' Leader of a Cellular mRNA", *Nature,* 353, 90–94, 1991.

McCafferty et al., "Phage Antibodies: Filamentous Phage Displaying Antibody Variable Domains", *Nature,* vol. 348, 552–554, 1990.

McCormack and Thompson, "Somatic Diversification of the Chicken Immunoglobulin Light–Chain Gene", *Advances in Immunology,* vol. 48, 41–67, 1989.

McCormack et al., "Avian B–Cell Development: Generation of an Immunoglobulin Repertoire by Gene Conversion", *Annu. Rev. Immunol.,* 9. 219–241, 1991.

McCormack et al., "Chicken IgL Gene Rearrangement Involves Deletion of a Circular Episome and Addition of Single Nonrandom Nucleotides to Both Coding Segments", *Cell,* vol. 56, 785–791, 1989.

McCormack et al., "Germ Line Maintenance of the Pseudogene Donor Pool for Somatic Immunoglobulin Gene Conversion in Chickens", *Molecular and Cellular Biology,* vol. 13:2, 821–830, 1993.

McCormack et al., "Selection for B cells with Productive IgL Gene Rearrangements Occurs in the Bursa of Fabricius During Chicken Embryonic Development", *Gene & Development,* 3:838–847, 1989.

Morrison, "Chimeric Human Antibody Molecules: Mouse Antigen–Binding Domains with Human Constant Region Domains", *Proc. Nat'l. Acad. Sci. USA,* vol. 81, 6851–6855, 1984.

Morrison, "Transfectomas Provide Novel Chimeric Antibodies", *Science,* 229, 1202–1207, 1985.

Morrison, "Transfer and Expression of Immunglobulin Genes", *Ann. Rev. Immunol.,* 2, 239–256, 1984.

Neuberger, "Expression and Regulation of Immunoglobulin Heavy Chain Gene Transfected into Lymphoid Cells", *The EMBO Journal,* vol. 2:8, 1373–1378, 1983.

Nishinaka et al., "A New Cell Line for the Production of Chicken Monoclonal Antibody by Hybridoma Technology", *Journal of Immunological Methods,* 139, 217–222, 1991.

Nishinaka et al., "Establishment of a Chicken x Chicken Hybridoma Secreting Specific Antibody", *Int. Arch. Allergy Appl. Immunol.,* 89, 416–419, 1989.

Orlandi et al., "Cloning Immunoglobulin Variable Domains for Expression by the Polymerase Chain Reaction", *Proc. Nat'l. Acad. Sci. USA.,* 86, 3833–3837, 1989.

Parvari et al., "Analyses of Chicken Immunoglobulin Light Chain cDNA Clones Indicate a Few Germline Vλ Genes and Allotypes of the Cλ Locus", *The EMBO Journal,* vol. 6:1, 97–102, 1987.

Parvari et al., Chicken Immunoglobulins γ–Heavy Chains: Limited VH Gene Repertorie, Combinatorial Diversification by D Gene Segments and Evolution of the Heavy Chain Locus, *The EMBO Journal,* vol. 7:3, 739–744, 1988.

Reynaud et al., "A Single Rearrangement Event Generates Most of the Chicken Immunoglobulin Light Chain Diversity", *Cell,* vol. 40, 283–291, 1985.

Reynaud et al., "Complete Sequence of a Chicken λ Light Chain Immunoglobulin Derived From the Nucleotide Sequence of its mRNA", *Proc. Nat'l. Acad. Sci. USA,* vol. 80, 4099–4103, 1983.

Reynaud et al., "Somatic Hyperconversion Diversifies the Single $V_H$ Gene of the Chicken with a High Incidence in the D Region", *Cell,* 59, 171–183, 1989.

Rich et al., "Expression of Cystic Fibrosis Transmembrane Conductance Regulator Corrects Defective Chloride Channel Regulation in Cystic Fibrosis Airway Epithelial Cells", *Nature,* vol. 347, 358–363, 1990.

Riordan et al., "Identification of the Cystic Fibrosis Gene: Cloning and Characterization of Complementary DNA", *Science,* 245, 1066–1073, 1989.

Sharon et al., "Expression of a $V_H C_K$ Chimaeric Protein in Mouse Myeloma Cells", *Nature,* vol. 309, 364–367, 1984.

Simon and Rajewsky, "Enhancer–Constitutive Vectors for the Expression of Recombinant Antibodies", *Nucleic Acids Research,* vol. 16:1, 354, 1988.

Song et al., "Antibodies to the α–Subunit of Insulin Receptor From Eggs of Immunized Hens", *The Journal of Immunology,* vol. 135:5, 3354–3359, 1985.

Tata et al., "Cloning the Mouse Homolog of the Human Cystic Fibrosis Transmembrane Conductance Regulator Gene", *Genomics,* 10, 301–307, 1991.

Thompson and Neiman, "Somatic Diversification of the Chicken Immunoglobulin Light Chain Gene is Limited to the Rearranged Variable Gene Segment", *Cell,* vol. 48, 369–378, 1987.

Thompson, "Creation of Immunoglobulin Diversity by Intrachromosomal Gene Conversion", *Reviews,* 8:12, 1992.

Weill et al., "Rearrangement of Chicken Immunoglobulin Genes Is Not An Ongoing Process in the Embryonic Bursa of Fabricius", *Proc. Nat'l. Acad. Sci. USA,* vol. 83, 3336–3340, 1986.

Whitsett et al., "Human Cystic Fibrosis Transmembrane Conductance Regulator Directed to Respiratory Epithelial Cells of Transgenic Mice", *Nature Genetics,* vol. 2, 13–20, 1992.

Winter and Milstein, "Man–Made Antibodies", *Nature,* vol. 349, 293–299, 1991.

Wong et al., "Appearance of β–lactamase Activity in Animal Cells Upon Liposome–Mediated Gene Transfer", *Gene,* 10, 87–94, 1980.

Woolley and Landon, "Comparison of Antibody Production to Human Interleukin-6 (IL–6) by Sheep and Chickens", *Journal of Immunological Methods,* 178, 253–265, 1995.

Wu et al., "Nucleotide Sequence of a Chromosomal Rearranged $\lambda_2$ Immunoglobulin Gene of Mouse", *Nucleic Acids Research,* vol. 10:13, 3831–3843, 1982.

Yamanaka et al., "Chicken Monoclonal Antibody Isolated by a Phage Display System", *The Journal of Immunology,* 157, 1156–1162, 1996.

Zhang et al., "Rearrangement and diversification of immunoglobulin light–chain genes in lymphoid cells transformed by reticuloendotheliosis virus", *Molecular And Cellular Biology,* 9:11, 4970–4976, 1989.

Nishinaka et al., "Two chicken B cell lines resistant to ouabain for the production of chicken monoclonal antibodies," *J. Vet. Med. Sci.,* 58(11):1053–1056, 1996.

International Search Report dated Aug. 14, 1998 (PCT/US97/21077)(ARSB:504P).

Michael et al., "Development of a method to produce chicken antibodies," *Jour. Cell. Biochem.,* 10(18D):192, 1994.

Heavy Chain Expression Vector

Chicken Heavy Chain PCR Primers

*leader*

4. ATC AGC CCA CTC GTC TCC CTC CTG CTC CTG GCC GCC CTG CCA G/

*L-V intron* gtgaggggcgctgtgggctctatggggctctcagcggggctctgcgggctcaatggggccaaggggggg

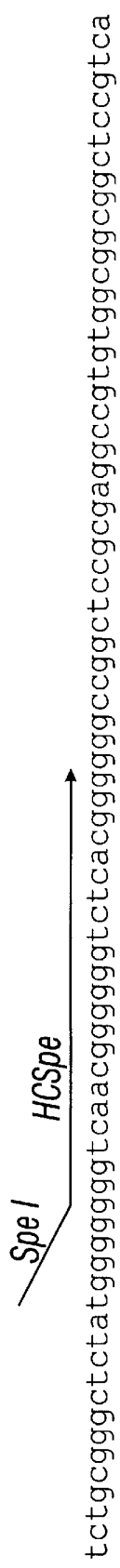

tctgcgggctctatgggggggtcaacgggggggtctcacgggggccgggggccgtgtggcggctccgtca

+1 gcgctctctgtcctcccccacag/ GG CTG ATG GCG GCC GTG ACG TTG GAC GAG TCC

*joining*

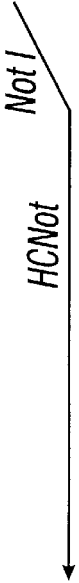

5. ACC GAA GTC ATC GTC TCC TCC G/ gtgagtcttcaaccccccaaaattgccgcggcgatttggg

FIG. 1A-2

Light Chain Expression Vector

Chicken Light Chain PCR Primers

*leader*

4. ATG GCC TGG GCT CCT CTC CTC CTG GCG GTG CTC GCC CAC ACC TCA G/

*ClaI* — *LVCla* → gtactcgttgcgcctgtcgggactgtgggcacgggctctgtcccattgctgcgcgggcagggctgtgctgtgcggggc

*L-V intron* cgtcactgattgccgtttctccctctccctctccag GT TCC CTG GTG CAG GCA GCG CTG

+1

*joining* ← *839Xho* *XhoI*

5. GGG ACA ACC CTG ACC GTC CTA G/ gtgagtcgctgacctcgtctcggtctttcttcccccatc

*FIG. 1B-2*

FIG. 4A CFTR 1 antibody
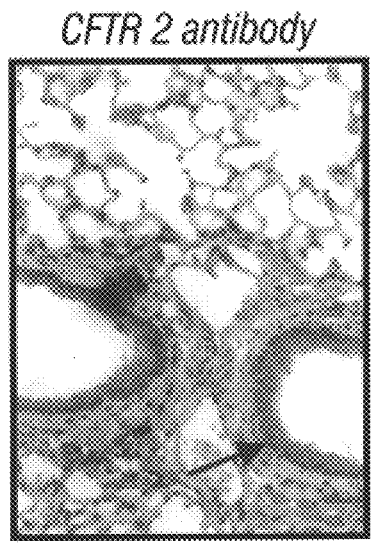
FIG. 4B CFTR 2 antibody
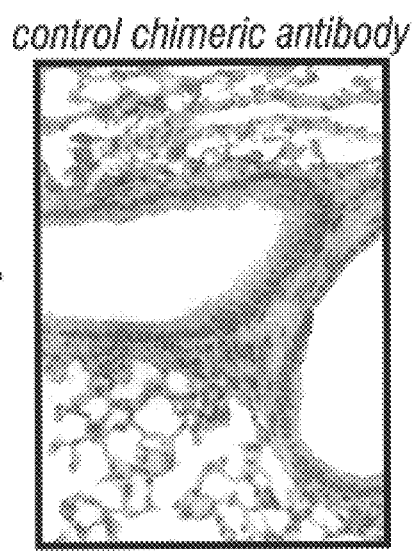
FIG. 4C control chimeric antibody
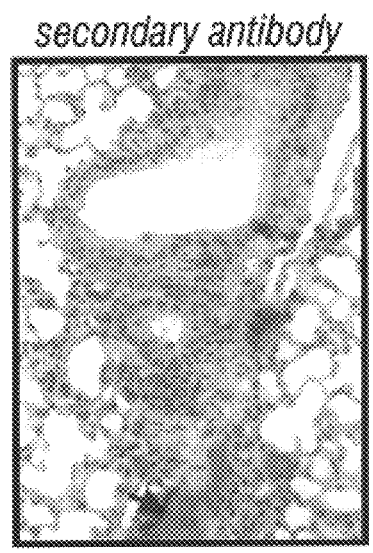
FIG. 4D secondary antibody

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
      (A) LENGTH: 14 base pairs
      (B) TYPE: nucleic acid
      (C) STRANDEDNESS: single
      (D) TOPOLOGY: linear (xi) SEQUENCE DESCRIPTION: SEQ ID NO:1:

GATCCGCGGC CGCG                                                       14

(2) INFORMATION FOR SEQ ID NO:2:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (xi) SEQUENCE DESCRIPTION: SEQ ID NO:2:

AAGGGGCTCA CACTAGTAGG CTTGAGG                              27

(2) INFORMATION FOR SEQ ID NO:3:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (xi) SEQUENCE DESCRIPTION: SEQ ID NO:3:

CCTCAAGCCA CTAGTGTGAG CCCCTT                               26

(2) INFORMATION FOR SEQ ID NO:4:

(i) SEQUENCE CHARACTERISTICS:
      (A) LENGTH: 14 base pairs
      (B) TYPE: nucleic acid
      (C) STRANDEDNESS: single
      (D) TOPOLOGY: linear (xi) SEQUENCE DESCRIPTION: SEQ ID NO:4:

AGCTTGCTCG AGCA                                                       14

(2) INFORMATION FOR SEQ ID NO:5:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (xi) SEQUENCE DESCRIPTION: SEQ ID NO:5:

GTGGGTATCG ATTGGCTGAT ATCCTGCA                                       28

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:6:

GGATATCAGC CAATCGATAC CCACTGCA                                       28

(2) INFORMATION FOR SEQ ID NO:7:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:7:

GGACTAGTGT CAACGGGGGG TCTCACGGGG GGCCGGCTC                            39

(2) INFORMATION FOR SEQ ID NO:8:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:8:

ATAAGAATGC GGCCGCGGCA ATTTTGGGGG GGGTTGAAGA CT                        42

(2) INFORMATION FOR SEQ ID NO:9:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:9:

CCATCGATGA CTGTGGGCAC GGGGCTCTGT CCCATTGCTG C                         41

(2) INFORMATION FOR SEQ ID NO:10:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:10:

CCGCTCGAGG GAAGAAAGAC CGAGACGAGG TCAGCGACT                            39

(2) INFORMATION FOR SEQ ID NO:11:

(i) SEQUENCE CHARACTERISTICS:
        (A) LENGTH: 126 amino acids
        (B) TYPE: amino acid
        (C) STRANDEDNESS:
        (D) TOPOLOGY: linear (xi) SEQUENCE DESCRIPTION: SEQ ID NO:11:

```
Met Ala Trp Thr Ser Leu Ile Leu Ser Leu Leu Ala Leu Cys Ser Gly
1               5                   10                  15

Ser Leu Val Gln Ala Ala Leu Thr Gln Pro Ser Ser Val Ser Ala Asn
            20                  25                  30

Pro Gly Gly Thr Val Lys Ile Thr Cys Ser Gly Asp Ser Ser Tyr Tyr
        35                  40                  45

Gly Trp Tyr Gln Gln Lys Ala Pro Gly Ser Ala Pro Val Thr Val Ile
    50                  55                  60

Tyr Asp Asn Thr Asn Arg Pro Ser Asn Ile Pro Ser Arg Phe Ser Gly
65                  70                  75                  80

Ser Lys Ser Gly Ser Thr Ala Thr Leu Thr Ile Thr Gly Val Arg Ala
                85                  90                  95

Asp Asp Asn Ala Val Tyr Tyr Cys Ala Ser Thr Asp Ser Ser Ser Thr
                100                 105                 110

Ala Xaa Gly Ile Phe Gly Ala Gly Thr Thr Leu Thr Val Leu
        115                 120                 125

(2) INFORMATION FOR SEQ ID NO:12:

(i) SEQUENCE CHARACTERISTICS:
        (A) LENGTH: 126 amino acids
        (B) TYPE: amino acid
        (C) STRANDEDNESS:
        (D) TOPOLOGY: linear (xi) SEQUENCE DESCRIPTION: SEQ ID NO:12:

Met Ala Trp Thr Ser Leu Ile Leu Ser Leu Leu Ala Leu Cys Ser Gly
1               5                   10                  15

Ser Leu Val Gln Ala Ala Leu Thr Gln Pro Ser Ser Val Ser Ala Asn
            20                  25                  30

Pro Gly Glu Thr Val Lys Ile Thr Cys Ser Gly Gly Ser Met Met Tyr
        35                  40                  45

Gly Trp Tyr Gln Gln Lys Ala Pro Gly Ser Ala Pro Val Thr Leu Ile
    50                  55                  60

Tyr Tyr Asn Ser Gln Arg Pro Ser Asp Ile Pro Ser Arg Phe Ser Gly
65                  70                  75                  80

Ser Leu Ser Gly Ser Thr Asn Thr Leu Thr Ile Thr Gly Val Gln Val
                85                  90                  95

Glu Asp Glu Ala Val Tyr Phe Cys Gly Ser Trp Asp Asn Ser Ala Gly
                100                 105                 110

Tyr Val Gly Ile Phe Gly Ala Gly Thr Thr Leu Thr Val Leu
        115                 120                 125

(2) INFORMATION FOR SEQ ID NO:13:

(i) SEQUENCE CHARACTERISTICS:
        (A) LENGTH: 125 amino acids
        (B) TYPE: amino acid
        (C) STRANDEDNESS:
        (D) TOPOLOGY: linear (xi) SEQUENCE DESCRIPTION: SEQ ID NO:13:

Met Ala Trp Thr Ser Leu Ile Leu Ser Leu Leu Ala Leu Cys Ser Gly
1               5                   10                  15

Ser Leu Val Glu Ala Glu Leu Ile Gln Pro Thr Ser Val Ser Ala Asn
            20                  25                  30

Pro Gly Glu Thr Val Lys Ile Thr Cys Ser Gly Asp Thr Ile Tyr Ile
        35                  40                  45
```

```
Gly Trp Tyr Gln Gln Lys Ala Pro Gly Ser Ala Pro Val Thr Val Ile
    50                  55                  60

Tyr Asp Asn Thr Thr Arg Pro Ser Asn Ile Pro Ser Arg Phe Ser Gly
65                  70                  75                  80

Ser Leu Ser Gly Ser Thr Asn Thr Leu Thr Ile Thr Gly Val Gln Val
                85                  90                  95

Glu Asp Glu Ala Val Tyr Phe Cys Ala Asn Ala Asp Ser Ser Ser Thr
                100                 105                 110

Ala Gly Ile Phe Gly Ala Gly Thr Thr Leu Thr Val Leu
            115                 120                 125

(2) INFORMATION FOR SEQ ID NO:14:

(i) SEQUENCE CHARACTERISTICS:
        (A) LENGTH: 124 amino acids
        (B) TYPE: amino acid
        (C) STRANDEDNESS:
        (D) TOPOLOGY: linear (xi) SEQUENCE DESCRIPTION: SEQ ID NO:14:

Met Ala Trp Thr Ser Leu Ile Leu Ser Leu Leu Ala Leu Cys Ser Gly
1               5                   10                  15

Ser Leu Val Gln Ala Ala Leu Thr Gln Pro Ala Ser Val Ser Ala Asn
                20                  25                  30

Pro Gly Glu Thr Val Glu Ile Thr Cys Ser Gly Asp Ser Ser Tyr Tyr
                35                  40                  45

Gly Trp Tyr Gln Gln Lys Ala Pro Gly Ser Ala Pro Val Thr Leu Ile
    50                  55                  60

Tyr Asp Asn Thr Asn Arg Pro Ser Asn Ile Pro Ser Arg Phe Ser Gly
65                  70                  75                  80

Ser Lys Ser Gly Ser Thr Ala Thr Leu Thr Ile Thr Gly Val Arg Ala
                85                  90                  95

Asp Asp Glu Gly Ile Tyr Tyr Cys Ala Ser Thr Asp Ser Ser Ser Thr
                100                 105                 110

Ala Ala Phe Gly Ala Gly Thr Thr Leu Thr Val Leu
            115                 120

(2) INFORMATION FOR SEQ ID NO:15:

(i) SEQUENCE CHARACTERISTICS:
        (A) LENGTH: 146 amino acids
        (B) TYPE: amino acid
        (C) STRANDEDNESS:
        (D) TOPOLOGY: linear (xi) SEQUENCE DESCRIPTION: SEQ ID NO:15:

Met Gly Trp Ser Cys Ile Met Leu Phe Leu Ala Ala Thr Ala Thr Gly
1               5                   10                  15

Leu Met Ala Ala Val Thr Leu Asp Glu Ser Gly Gly Gly Leu Gln Thr
                20                  25                  30

Pro Gly Arg Ala Leu Ser Leu Val Cys Lys Ala Ser Gly Phe Thr Phe
                35                  40                  45

Ser Ser Tyr Asn Met Gly Trp Val Arg Gln Ala Pro Gly Lys Gly Leu
    50                  55                  60

Glu Phe Val Ala Gly Ile Asp Asn Thr Gly Arg Tyr Thr Gly Tyr Gly
65                  70                  75                  80

Ser Ala Val Lys Gly Arg Ala Thr Ile Ser Arg Asp Asn Gly Gln Ser
                85                  90                  95
```

Thr Val Arg Leu Gln Leu Asn Asn Leu Arg Ala Glu Asp Thr Gly Thr
            100                 105                 110

Tyr Tyr Cys Ala Lys Ala Ala Gly Ser Ala Tyr Gly Cys Gly Ala Tyr
            115                 120                 125

Thr Ala Gly Ser Ile Asp Ala Trp Gly His Gly Thr Glu Val Ile Val
            130                 135                 140

Ser Ser
145

(2) INFORMATION FOR SEQ ID NO:16:

(i) SEQUENCE CHARACTERISTICS:
        (A) LENGTH: 145 amino acids
        (B) TYPE: amino acid
        (C) STRANDEDNESS:
        (D) TOPOLOGY: linear (xi) SEQUENCE DESCRIPTION: SEQ ID NO:16:

Met Gly Trp Ser Cys Ile Met Leu Ser Leu Ala Ala Thr Ala Thr Gly
1               5                   10                  15

Leu Met Ala Ala Val Thr Leu Asp Glu Ser Gly Gly Gly Leu Gln Thr
            20                  25                  30

Pro Arg Gly Ala Leu Ser Leu Val Cys Lys Ala Ser Gly Phe Thr Phe
            35                  40                  45

Ser Tyr Leu Met His Trp Val Arg Gln Ala Pro Gly Lys Gly Leu Glu
    50                  55                  60

Trp Val Gly Gly Ile Arg Ser Asp Gly Ser Lys Thr Gly Tyr Gly Ala
65                  70                  75                  80

Ala Val Lys Gly Arg Ala Thr Ile Ser Arg Asp Asn Gly Gln Ser Thr
            85                  90                  95

Val Arg Leu Gln Leu Asn Asn Leu Arg Ala Glu Asp Thr Ala Thr Tyr
            100                 105                 110

Tyr Cys Ala Lys Glu Ser Gly Ser Gly Gly Ser Thr Gly Ser Ser Tyr
            115                 120                 125

Ala Ala Asn Ile Asp Ala Trp Gly His Gly Thr Glu Val Ile Val Ser
            130                 135                 140

Ser
145

(2) INFORMATION FOR SEQ ID NO:17:

(i) SEQUENCE CHARACTERISTICS:
        (A) LENGTH: 141 amino acids
        (B) TYPE: amino acid
        (C) STRANDEDNESS:
        (D) TOPOLOGY: linear (ix) FEATURE:
        (A) NAME/KEY: Protein
        (B) LOCATION: 1..2
        (D) OTHER INFORMATION: /product= "OTHER"
            /note= "x = any amino acid"

(xi) SEQUENCE DESCRIPTION: SEQ ID NO:17:

Met Gly Trp Ser Cys Ile Met Leu Ser Leu Ala Ala Thr Ala Thr Gly
            -125                -120                -115

Leu Met Ala Ala Val Thr Leu Asp Glu Ser Gly Gly Gly Leu Gln Thr
            -110                -105                -100

Pro Gly Gly Gly Leu Ser Leu Val Cys Lys Ala Ser Gly Phe Thr Phe

```
                -95                  -90                   -85
Ser Ser Asn Gly Met Gly Trp Val Arg Gln Ala Pro Gly Lys Gly Leu
-80             -75                  -70             -65

Glu Tyr Val Ala Gly Ile Ser Ser Gly Lys Tyr Thr Gly Tyr Gly
            -60             -55             -50

Ser Ala Val Lys Gly Arg Ala Thr Ile Ser Arg Asp Asn Gly Gln Ser
            -45             -40             -35

Thr Val Arg Leu Gln Leu Asn Asn Leu Arg Ala Glu Asp Thr Ala Thr
            -30             -25             -20

Tyr Tyr Cys Ala Lys Gly Gly Arg Ser Gly Phe Thr Cys Val Ile Ser
            -15             -10              -5

Xaa Thr Trp Gly His Gly Thr Glu Val Ile Val Ser Ser
1                5                   10
```

(2) INFORMATION FOR SEQ ID NO:18:

(i) SEQUENCE CHARACTERISTICS:
        (A) LENGTH: 147 amino acids
        (B) TYPE: amino acid
        (C) STRANDEDNESS:
        (D) TOPOLOGY: linear (xi) SEQUENCE DESCRIPTION: SEQ ID NO:18:

```
Met Gly Trp Ser Cys Ile Met Leu Phe Leu Ala Ala Thr Ala Thr Gly
1                5                  10                  15

Leu Met Ala Ala Val Thr Leu Asp Glu Ser Gly Gly Gly Leu Gln Thr
            20                  25                  30

Pro Gly Gly Ala Leu Ser Leu Val Cys Leu Gly Ser Gly Phe Asp Phe
            35                  40                  45

Ser Ser Thr Asp Met Gly Trp Val Arg Gln Ala Pro Gly Lys Gly Leu
50                  55                  60

Glu Phe Val Ala Gly Ile Tyr Ser Thr Pro Ser Gly Thr Gly Tyr Ala
65                  70                  75                  80

Pro Ala Val Arg Gly Arg Ala Thr Ile Ser Arg Asp Asn Gly Gln Ser
            85                  90                  95

Thr Leu Arg Leu Gln Leu Asn Asn Leu Arg Ala Glu Asp Thr Gly Thr
            100                 105                 110

Tyr Tyr Cys Ala Lys Ala Ala Gly Ser Gly Tyr Cys Ser Ser Asp Ala
            115                 120                 125

Thr Ile Ala Gly Ser Ile Asp Ala Trp Gly His Gly Thr Glu Val Ile
            130                 135                 140

Val Ser Ser
145
```

(2) INFORMATION FOR SEQ ID NO:19:

(i) SEQUENCE CHARACTERISTICS:
        (A) LENGTH: 13 amino acids
        (B) TYPE: amino acid
        (C) STRANDEDNESS:
        (D) TOPOLOGY: linear (xi) SEQUENCE DESCRIPTION: SEQ ID NO:19:

```
Lys Glu Glu Thr Glu Glu Glu Val Gln Asp Thr Arg Leu
1                5                  10
```

(2) INFORMATION FOR SEQ ID NO:20:

(i) SEQUENCE CHARACTERISTICS:

(A) LENGTH: 13 amino acids
        (B) TYPE: amino acid
        (C) STRANDEDNESS:
        (D) TOPOLOGY: linear (xi) SEQUENCE DESCRIPTION: SEQ ID NO:20:

Lys Glu Glu Thr Glu Glu Val Gln Glu Thr Arg Leu
1               5                   10

(2) INFORMATION FOR SEQ ID NO:21:

(i) SEQUENCE CHARACTERISTICS:
        (A) LENGTH: 5526 base pairs
        (B) TYPE: nucleic acid
        (C) STRANDEDNESS: single
        (D) TOPOLOGY: linear (xi) SEQUENCE DESCRIPTION: SEQ ID NO:21:

| | | | | | |
|---|---|---|---|---|---|
| GCAGGTGGTT | CAAGAAACGT | TTAGATGTTG | TACTGAGGGA | TGTGGTTTAG | TGGGAAATAC | 60 |
| TGGTGATAGG | TGGATGGTTG | GACTGGAGGA | TCTTAGAGGT | CTTTTCCAAC | CTTGGTGATT | 120 |
| ATGTGATTCT | ATGAAGGGAG | CCATAGCCTG | CTCCCATCAT | GCCCCGCCAG | TCCGGCTCTC | 180 |
| CCGAGCACTT | TGGTTCCGCA | GCATCCAGGC | CGCTCTGGGG | CCGGTGTGGG | CCTGGGTGCT | 240 |
| GCCACGTGTC | CCCGCTGCAA | GGCCTGGCCA | ACCCCGCTGT | GCCACAGTGC | AGGGGCTGGG | 300 |
| CAGGAGTGGG | CAGGGAGGTG | TGGGGAGAGG | CGTAGGACGT | GGCTGGGAGC | GCAGGGAGTT | 360 |
| ATTTGCATAG | GGGGCGTGC  | TGCGGAAGGA | CGCGGGTATA | AAAGGGCATC | GAGGTCCCCG | 420 |
| GCACAGCCCC | ATCGGCGTGG | GGACACACAG | CTGCTGGGAT | TCCGCCATGG | CCTGGGCTCC | 480 |
| TCTCCTCCTG | GCGGTGCTCG | CCCACACCTC | AGGTACTCGT | TGCGCCTGGT | CGGGGACTGT | 540 |
| GGGCACGGGG | CTCTGTCCCA | TTGCTGCGCG | GGCAGGGCTG | TGCGTGCGGG | GCCGTCACTG | 600 |
| ATTGCCGTTT | TCTCCCCTCT | CTCCTCTCCC | TCTCCAGGTT | CCCTGGTGCA | GGCAGCGCTG | 660 |
| ACTCAGCCGT | CCTCGGTGTC | AGCAAACCCG | GGAGAAACCG | TCAAGATCAC | CTGCTCCGGG | 720 |
| GATAGGAGCT | ACTATGGCTG | GTACCAGCAG | AAGGCACCTG | GCAGTGCCCC | TGTCACTGTG | 780 |
| ATCTATGCTA | ACACCAACAG | ACCCTCGGAC | ATCCCTTCAC | GATTCTCCGG | TTCCAAATCC | 840 |
| GGCTCCACAG | CCACATTAAC | CATCACTGGG | GTCCAAGCCG | ACGACGAGGC | TGTCTATTAC | 900 |
| TGTGGGAGTG | CAGACAGCAG | CAGTACTGCT | GCACGGTGAC | ACAAAGCAAT | GGGGAAATGA | 960 |
| TACAAAAACC | TCCTGCCAGT | GCAAGGAGCA | GCTGATGGTT | TTTACTGTCT | CTGTCTTACA | 1020 |
| AGTCCCACCT | CCATTCCTGC | CCTGTGCTGC | AGCGCCCGGG | TCCTCCTGCG | TTCCCAGGCT | 1080 |
| GCACCCCAGG | TCCAGCTGGC | TGAATCCCTG | CCATCCAACA | TCCACCATTT | GTAGTGTCCC | 1140 |
| CTGCATGCAC | CAGGCTGGCA | GCTCCTCATC | TGCTCCTGCT | CCCACTGAGA | CCACCTGCCC | 1200 |
| AGCCCATGCT | GGAGGGCCAC | CACCACTCAA | TTGCACTGTA | CATCAGCACA | GCACCAGTTC | 1260 |
| TCTTACATGT | GTCCCTCTGA | GGAAAAGAGC | TGGACTTCTA | AGCACCCTTA | GTGTACTCAC | 1320 |
| CTAAAATGAA | ACTGAAACCC | CATAAAAGTC | TCAGAAATAC | CCAGAAACTG | TTCATCCATA | 1380 |
| GTATATGGCA | TCAACTTTAG | CTATATACTT | TTCATAGATA | GTTTCAATGA | GTTTCTATCA | 1440 |
| CTTGCACCGG | TCACTTGCAC | CTAAGCCTTC | CCAGAGGAAA | ACCAAACCTT | TGAAACAGAA | 1500 |
| AGTACTTCCA | ACCACAAAAT | CTTTGATGCA | TCATTCATTT | GCTAGTGACT | CAGGAGATTC | 1560 |
| ACCAACTCTG | CCTCTTTCTA | TAACCACTTG | CACAAACCAC | AGCATTTGCA | TATTTGTGAG | 1620 |
| TTTATTTTTA | AGCCAGTGCC | TTGGCTCTGG | CAGCTCTGGT | TGGGCATCAA | CATCCTCTTC | 1680 |
| ACATTTTCTT | TTCCTCTCTT | GAGGAGGATG | TGGGCAGCAT | GTGCAGCGCA | GTGGTGCACC | 1740 |

-continued

```
AATGGGATAA AGCTGGGCCC AGTGACCTCG AAGGACAACA TCAGCGAGAG TAAGGCCATC    1800

AAAACAGACA GGCCTGAATT GGAGGGGCTG CACTAAAACT GGATGACAGG CAAGAACATT    1860

ATTTGGTGGG TTCTTGTGGC AGGTTGACAT GACTTCGGCC AAGACCTTGA CCAACAATGG    1920

CACAGCTACT GGATATCCCT TGGAAGAGGT GAGGAGGACA CACAGACACC ATCTACACTC    1980

TGTGACCCAC AGCAGGCAGC AGGGCTCAGC CACACATGCG CGGGCATGGG CCGCTGCTTG    2040

GGCTGTTTCT GCACGGCCAT GTATCACTGC AGGTATTTCC CCGGTGGGAC CTCAGGAATC    2100

AACTGATTGT CCTCAGGAAG TCGCTCTGTG TTCACTTACA GTCCTCCCCA GCAGTAAGTG    2160

GGTGCTCAGG CTCCTCACAG CCTTTGTTTG TTTTTTTTTT TTTTGGTTGG TTGGTGGGGC    2220

TTTGTCCAAC TTTGGCTGTG GCAGTAGATC CTTGGTCTGC CTAGCCACAC TGAAATGTAC    2280

TCATGCACCT TTCCCTGATT TGCAGAAAGA AGGTTGTATG GTCTGAATGC TCTGTGCTGT    2340

TGCAAGTCTC TTCTGGTTCT TCGAAATCTG CAGAGTCCCT CCCGACTGTG TCCTTGGTAC    2400

TGAACATCCT TGTTCACCGT GTCAGAAGGA AGATGGGGGG CTGGAGGCAG TAGTGCGTGG    2460

CACCAGGATC CCCTGGGGCA TTTCTTGCCT GCGGCGCCTG GGTGCTCCGC GTGGCTGCCA    2520

GGGGACACA CCTCCTGTAC CAGCCCCCAG CACCACCATC CTGCTGTGTC CATTCCGTCA    2580

CCTTGATCCT ACTGTGTCCA GCCCATCGTC TCCCTTCTGC TTTGCCCGTC AGAACACTTC    2640

CATCCCATCA CTTCTGACCC ACCCCCTCAT CCTGCCGCCT CCACAGGACC CAGAACTGCC    2700

CCTGCCACGA AGTGGGAGGT TTTTGCATTG CTCCGTATCA CTGTGTGGTA TATTTGGGGC    2760

CGGGACAACC CTGACCGTCC TAGGTGAGTC GCTGACCTCG TCTCGGTCTT TCTTCCCCCA    2820

TCGTGAAATT GTGACATTTT GTCGATTTTT GGTGATTTGG GGGTTTTTCT TGGACTTGGC    2880

GGCAGGCTGG GGTCTGCCAC CGGCGCAGGG CCGGGCACTC AGCGCGGCAG CCTGGGCTGA    2940

GTCTTGTCCC CACCGAGCCG GAGGGCTCCG GTGTGCGCCA TGGAGGACTT AGGGTTATTT    3000

TGTCAATGGA AAGTTCTTAA AATTTGACCA GAAAATGTGC CCGAGGTCTG TCTCTGCCAC    3060

ACAATTTCAG AAATTGTGTC TAGGTCGATG AGAAGACAGT TTTTGTCTTT GTCAGGAAAT    3120

TAGTTGTGAG TTGTTAGTCC TTCCCTCTTA GTCCTAAGGA CTAAGACCTT TGTCCCCGGT    3180

CTGGTCTCTC ACTGGGGACT CTTGGCTCCA GTGCCATGGG GAGCCCAAGT GTCACTGACA    3240

CAGTGTCCTT GGGGGTGAAA TTCAGTTTTT CAGCTGTCCA GGTAAGTGCT GTCAAAAAAT    3300

GGAGGTTATT CTGCTGAAAA AGCTGAGAGG AATATTTTGT CATTTTTTTC GGAAATATAT    3360

ATATATATAT ATATATAAAT ATATAAATTA TTTATATATT TTATATATAT ATATATAAA    3420

AATATATGTA TTTCTCTCTT TCTTTTTATA TATATATATA AATATATATA TATTTCTCCC    3480

TCTTTCTTTA TATATATTTA TAGGGAGAGA ATCTATATTT TGGCCAATTT GGCCAATTTC    3540

TCTCTCTCTC TCTTTATATA TATATATATA TATATATGTA ATTTATATAT ATATATATAA    3600

ATTTATATTT ATTTATTTAT TTATTTATAT AGATTATTTT TATATACATA TATATATATA    3660

AATTTGGCCA ATTTAGAAGA AATTGGCCAA AAAAACCCAA TCTGAACCAA ATTACTTAGG    3720

GCATAAGTCC AAAAAAAAAG TGCAGTTCAA GAATTCCTCG CTGGAAAGTT TTTAATGGGG    3780

GCAGTTCTTC CCCATTTTCT GGTGTAGATA TGAGTGAAGA TATAGATATG TATGTAGATA    3840

TAGATTTGGC TATAGTTTGT TTGATGAACA GTCTGAGGAA GAGTAAATCT TGCCTTCCTC    3900

ATGGCAATTT TTAATTCTAC TTCTTCTGAG ACAAGTCTGA ACATGCCTTG AGGTAGAAAG    3960

AGCCCGAAAA TTGAGTGCTT TTTCTTTGAA ATTTTAATTA AAATTAAAAA ATAGCCTTAC    4020

AGCAGGAAAG AAAGGGGGTG ATGGCAGCTA ATCGGAGTTC CAAAGCTGAA CCACGTTCAC    4080

CCAAACACGT GGTTGAAATT TTGTGTGTGT ATATATATAA ATATATATAT GTATACAAAA    4140
```

```
GAAAATGCCT ATATATAAAA AAATTGTTAT GTATATTATA TAGATTTATT ATAGATATGT      4200

ACATAAGATA TAACACGTAT ACATATATAT GTAGTCTGCT GTATGCTTTG TATAAATTTT      4260

TATAGATATG ATGTATATTA TATGCATGGG TTATATATCT ATAATATATT TTATCTGTAG      4320

AAGGAACTAC AGTATAAAAT GCATATATGC GTATATATAC ACATATTTAT ATATATGTGT      4380

ATATATATGT ATACGCACAC GTATAACATC CATGAAAATA GATATGGATG GGTGGATGTG      4440

TTTGTTTTAC AGAGGTGCAT GTGTGTCTGT ACATACACAG CCATACATAC GCGTGTGGCC      4500

GCTCTGCCTC TCTCTTGCAG GCCAGCCCAA GGTGGCCCCC ACCATCACCC TCTTCCCACC      4560

GTCAAAGGAG GAGCTGAACG AAGCCACCAA GGCCACCCTG GTGTGCCTGA TAAACGACTT      4620

CTACCCCAGC CCAGTGACTG TGGATTGGGT GATCGATGGC TCCACCCGCT CTGGCGAGAC      4680

CACAGCACCA CAGCGGCAGA GCAACAGCCA GTATATGGCC AGCAGCTACC TGTCACTGTC      4740

TGCCAGCGAC TGGTCAAGCC ACGAGACCTA CACCTGCAGG GTCACACACA ACGGCACCTC      4800

TATCACGAAG ACCCTGAAGA GGTCCGAGTG CTAATAGTCC CACTGGGGAT GCAATGTGAG      4860

GACAGTGGTT CCTCACCCTC CCTGTCCCTC TGGGCCGCTG CTGGTGGCAG CAGCCCTCAC      4920

TTCCCACTCA GATGTCCCCC ACCGTGCCCC CATCACCCAC CTCTGCCTGT CGACTCCTCT      4980

TGCCCTCATC TCTCCAGGTG TCACATTAAT AAACACGACA CTGAACTAGT GCTGACTCTG      5040

CATCCATGTC TCTGTGTCCT TTTGCGTGCT GTCTGCATCT CACACAGGGG GGTCGGCCCA      5100

GTATGGGGAA GGGCTGGGGG GCGCATACAC ACATATTGGT AATGTTGGGG GCGGGGGGGG      5160

GGGGGTGGGG GGGTCAACAG ATCAGCACTG GAGACACTGG TGTATACCCT GGCACCACCA      5220

ACATCTAAGG CAGGGTGCTT TGGGGCAATT TTGGGGCAGT TTAAGGTCTG TGCTGGCACT      5280

GAGCACGTGG CTGTGGCCGT GCTGTCCTCA TCTCCCACCC ACTACGGTCT GTGCGCCAGG      5340

TCCCTAGCAG AGATTTGCTT TATGCTGGGA ACAGGGGGAG TTCTGGCTCT GTTCCCTTGC      5400

ATTCAGACAC CCTGGTGCCC CCTGGGTGGG ATGTCAGTGT GAATACTCCT TTGTGCCCTG      5460

TGCCTGCAGC AGCCTGACCC TCCACACACC ACGACCTT GTGTGCACCC CACCCCTGTC       5520

ACTATC                                                                5526
```

(2) INFORMATION FOR SEQ ID NO:22:

(i) SEQUENCE CHARACTERISTICS:
        (A) LENGTH: 229 amino acids
        (B) TYPE: amino acid
        (C) STRANDEDNESS:
        (D) TOPOLOGY: linear (xi) SEQUENCE DESCRIPTION: SEQ ID NO:22:

```
Met Ala Trp Ala Pro Leu Leu Leu Ala Val Leu Ala His Thr Ser Gly
 1               5                  10                  15

Ser Leu Val Gln Ala Ala Leu Thr Gln Pro Ser Ser Val Ser Ala Asn
            20                  25                  30

Pro Gly Glu Thr Val Lys Ile Thr Cys Ser Gly Asp Arg Ser Tyr Tyr
        35                  40                  45

Gly Trp Tyr Gln Gln Lys Ala Pro Gly Ser Ala Pro Val Thr Val Ile
    50                  55                  60

Tyr Ala Asn Thr Asn Arg Pro Ser Asp Ile Pro Ser Arg Phe Ser Gly
65                  70                  75                  80

Ser Lys Ser Gly Ser Thr Ala Thr Leu Thr Ile Thr Gly Val Gln Ala
                85                  90                  95

Asp Asp Glu Ala Val Tyr Tyr Cys Gly Ser Ala Asp Ser Ser Ser Thr
```

```
            100                 105                 110
Ala Gly Ile Phe Gly Ala Gly Thr Thr Leu Thr Val Leu Gly Gln Pro
            115                 120                 125
Lys Val Ala Pro Thr Ile Thr Leu Phe Pro Pro Ser Lys Glu Glu Leu
            130                 135                 140
Asn Glu Ala Thr Lys Ala Thr Leu Val Cys Leu Ile Asn Asp Phe Tyr
145                 150                 155                 160
Pro Ser Pro Val Thr Val Asp Trp Val Ile Asp Gly Ser Thr Arg Ser
                165                 170                 175
Gly Glu Thr Thr Ala Pro Gln Arg Gln Ser Asn Ser Gln Tyr Met Ala
                180                 185                 190
Ser Ser Tyr Leu Ser Leu Ser Ala Ser Asp Trp Ser Ser His Glu Thr
            195                 200                 205
Tyr Thr Cys Arg Val Thr His Asn Gly Thr Ser Ile Thr Lys Thr Leu
    210                 215                 220
Lys Arg Ser Glu Cys
225

(2) INFORMATION FOR SEQ ID NO:23:

(i) SEQUENCE CHARACTERISTICS:
        (A) LENGTH: 215 base pairs
        (B) TYPE: nucleic acid
        (C) STRANDEDNESS: single
        (D) TOPOLOGY: linear (xi) SEQUENCE DESCRIPTION: SEQ ID NO:23:

GTTGGATGGC CAAAAAACGG TTGTTTTTTT TTTTTTTTAA CCAAAATGGG CGGTTTTCGC        60

CCGAAAAGAG TGGGTGGAGT TTTTGGGTGA AAAAAGGCGG ATTTTGGGGC ATTGTGGTAC       120

TGCTGGTAGC ATCGACGCAT GGGGCCACGG GACCGAAGTC ATCGTCTCCT CCGGTGAGTC       180

TTCAACCCCC CCCAAAATTG CCGCGGCGAT TTTGG                                  215

(2) INFORMATION FOR SEQ ID NO:24:

(i) SEQUENCE CHARACTERISTICS:
        (A) LENGTH: 710 base pairs
        (B) TYPE: nucleic acid
        (C) STRANDEDNESS: single
        (D) TOPOLOGY: linear (xi) SEQUENCE DESCRIPTION: SEQ ID NO:24:

ACGCGCTAAC GAAGCCGGAG CCCTCCTTAT GCAAATTAGC CCCTCCAGAG GGCCATAAAA        60

GCGCCGGCTC TCCGACGGAG GAGCACCAGT CGGCTCCGCA ACCATGAGCC CACTCGTCTC       120

CTCCCTCCTG CTCCTGGCCG CCCTGCCAGG TGAGGGCGCT GTGGGCTCT ATGGGCTCT        180

ATGGGTCTC AGCGGGGCTC TGCGGGCTCA ATGGGGCCA AAGGGGGGT CTGCGGGCTC        240

TATGGGGGGG TCAACGGGGG GTCTCACGGG GGGCCGGCTC CGCGAGGCCG TGTGGCGGCG       300

GCTCCGTCAG CGCTCTCTGT CCTTCCCCAC AGGGCTGATG GCGGCCGTGA CGTTGGACGA       360

GTCCGGGGGC GGCCTCCAGA CGCCCGGAAG AGCGCTCAGC CTCGTCTGCA AGGCCTCCGG       420

GTTCACCTTC AGCAGTTACA ACATGGGTTG GGTGCGACAG GCGCCCGGCA AGGGGCTGGA       480

GTTCGTCGCT GGTATTGACA ACACTGGTAG ATACACAGGC TACGGGTCGG CGGTGAAGGG       540

CCGTGCCACC ATCTCGAGGG ACAACGGGCA GAGCACAGTG AGGCTGCAGC TGAACAACCT       600

CAGGGCTGAG GACACCGGCA CCTACTACTG CGCCAAAGCT GCTGGTCACG GTGACACCGA       660

TCCCCAGCAC GGGTGGCACA AAACCCACCG TTGCAACCCA AGGCGGTGAA                  710
```

(2) INFORMATION FOR SEQ ID NO:25:

(i) SEQUENCE CHARACTERISTICS:
        (A) LENGTH: 120 amino acids
        (B) TYPE: amino acid
        (C) STRANDEDNESS:
        (D) TOPOLOGY: linear (xi) SEQUENCE DESCRIPTION: SEQ ID NO:25:

```
Met Ser Pro Leu Val Ser Ser Leu Leu Leu Ala Ala Leu Pro Gly
 1               5                  10                  15

Leu Met Ala Ala Val Thr Leu Asp Glu Ser Gly Gly Gly Leu Gln Thr
                20                  25                  30

Pro Gly Arg Ala Leu Ser Leu Val Cys Lys Ala Ser Gly Phe Thr Phe
            35                  40                  45

Ser Ser Tyr Asn Met Gly Trp Val Arg Gln Ala Pro Gly Lys Gly Leu
        50                  55                  60

Glu Phe Val Ala Gly Ile Asp Asn Thr Gly Arg Tyr Thr Gly Tyr Gly
65                  70                  75                  80

Ser Ala Val Lys Gly Arg Ala Thr Ile Ser Arg Asp Asn Gly Gln Ser
                85                  90                  95

Thr Val Arg Leu Gln Leu Asn Asn Leu Arg Ala Glu Asp Thr Gly Thr
                100                 105                 110

Tyr Tyr Cys Ala Lys Ala Ala Gly
            115                 120
```

METHODS FOR THE PRODUCTION OF CHICKEN MONOCLONAL ANTIBODIES

This is a continuation of co-pending application Ser. No. 08/751,359 filed Nov. 18, 1996.

BACKGROUND OF THE INVENTION

The government may own rights in this application pursuant to grants from The National Institutes of Health including grant number R37 CA 48023

I. Field of the Invention

The present invention relates generally to the field of cellular and molecular immunology. In particular, the present invention relates to the production of monoclonal antibodies in an avian system, e.g., chickens.

II. Related Art

Monoclonal antibodies are valuable tools in basic research and have growing importance for medical diagnosis and therapy. The procedures for making monoclonal antibodies routinely use immunized mice, rats, hamsters or rabbits as the source of antibody producing B cells. Isolated B cells are fused to a nonsecreting, immortalized cell line, and then selected and screened for specific antibody production. A hybridoma will secrete a single monoclonal antibody indefinitely (Kohler and Milstein, 1974). Hybridoma technologies have important limitations, however. In particular, it has been difficult to make antibodies to some proteins and other antigens; it is hypothesized that these molecules have highly conserved epitopes that are not recognized as "foreign" making them less immunogenic in closely related species (Cinader, 1960).

Distinctive features of chicken immunology can be used to advantage to address some of these problems. Chickens can mount an effective immune response to highly conserved mammalian proteins and produce high affinity antibodies (Horton et al., 1984; Larsson et al., 1993). Polyclonal antibodies to calf thymus RNA polymerase II (Carroll and Stoller, 1983) and to the (x-subunit of the rat insulin receptor (Song et al., 1985) were easily made in the chicken; the same antigens were not effective at inducing specific antibody production in the rabbit. Chicken antibodies to 1,25-dihydroxyvitamin D were more specific and less cross-reactive than rabbit antibodies (Bauwens et al., 1987), making it likely that the chicken is recognizing different epitopes. Chicken antibodies made by individual investigators and harvested from egg yolk have been used to study human insulin (Lee et al., 1991), human plasma kallikein (Burger et al., 1985), IL-6 (Wooley et al., 1995), prostaglandins (Fertel et al., 1981) and PCNA (Gassman et al., 1990). In addition, chicken serum containing polyclonal antibodies to human complement components, human erthropoietin, fibrinogen and fibronectin are commercially available (American Research Products, Inc. 1995 Catalogue). However, there is not yet a reliable way to produce chicken monoclonal antibodies given the tendency of chicken cell lines to cease antibody production after a short period of time (Nishinaka et al., 1989, 1991).

Another approach to generating unique antibody sequences recently has developed. It now is possible to clone DNA encoding a specific antibody's heavy and light chains, and to express the cloned antibody chains following transfection into other eukaryotic cells (Neuberger et al., 1983; Gilles et al., 1983). Like hybridomas, these transfected cells can be selected, screened and cloned as stable transfectomas that secrete a monoclonal antibody (Sharon et al., 1984; Morrison, 1985). In addition, the ability to clone the DNA of individual leader (L), variable (V), diversity (D) and joining (J) gene segments (Larrick et al., 1989; Orlandi et al., 1989; Heinrichs et al., 1995) and to manipulate these domain segments by specific mutation and random combination has facilitated the engineering of "artificial" antibody combining sites to a variety of epitopes that can be expressed in transfectomas or by phage display (McMafferty et al., 1990; Winter and Milstein, 1991; Huston et al., 1988; Yamanaka et al., 1996)). These techniques have proved successful in producing monoclonal antibody-type reagents with new specificities and with modified effector functions. Even where successful immunization with a given antigen can be achieved, however, it is technically challenging to identify, and then clone, the heavy and light chain sequences encoding the specific antibody (see Antibody Engineering Chapters 2, 3, 6 Borrebaeck).

Thus, it is clear that there remains a need for improved methods for the production of monoclonal antibodies against epitopes conserved in mammalian species. In addition, there is a need for improved methods in the cloning and manipulation of immunoglobulin genes in various animal species, and in particular, avian species such as chicken.

SUMMARY OF THE INVENTION

It is a goal of the present invention to provide methods for producing antibodies against a variety of antigens, including mammalian antigens with highly conserved epitopes. In addition, it is a goal of the present invention to provide improved methods and compositions for the cloning and manipulation of immunoglobulin genes.

Thus the present invention provides methods for generating monoclonal antibodies comprising the steps of immunizing a chicken with an antigen composition, isolating B cells from the chicken; immortalizing the B cells; selecting an immortalized antibody producing B cell and preparing nucleic acids encoding the antigen binding exons of the light and heavy chain genes thereof; cloning the heavy and light chain antigen binding regions, respectively, into vectors encoding the constant and leader regions of an immunoglobulin heavy chain, the constant and leader regions of an immunogloblin light chain; transferring the vectors into a suitable host cell; culturing the host cell; and isolating antibodies produced by the cell.

In preferred embodiments, the immortalizing comprises fusing the B cells to a chicken lymphoblastoid cell line. In other preferred embodiments, the immortalizing comprises infection of the B cells with an avian retrovirus.

In particular aspects of the invention, the preparing nucleic acids comprises isolating nucleic acids from the B cell and conducting PCR amplification of the coding sequences for the heavy and light chain antigen binding regions. In particular embodiments, the isolated nucleic acids primarily comprise genomic DNA. In preferred aspects it is contemplated that the heavy chain PCR primers have the sequence of SEQ ID NO:7 and SEQ ID NO:8. In other embodiments the light chain PCR primers have the sequence of SEQ ID NO:9 and SEQ ID NO: 10.

In certain embodiments the antigen composition comprises an antigen selected from the group consisting of CFTR, transforming growth factor beta, transcription factors, DNA binding molecules; cyclin dependent kinases and RNA binding proteins and a pharmaceutical buffer carrier or diluent. In other preferred embodiments, the antigen composition comprises an antigen selected from the group consisting of lipids, phospholipids and carbohydrates and a pharmaceutical buffer carrier or diluent.

In other embodiments of the present invention, it is contemplated that the selecting comprises screening the B cells for production of an antibody of interest. In preferred embodiments, the screening comprises measuring the binding of the antibodies to a target antigen. In particular embodiments, the measuring is performed by a method selected from the group consisting of ELISA, Western blot and immune precipitation.

In preferred embodiments, it is contemplated that the host cell is a murine myeloma line. In other preferred embodiments, the culturing performed in vitro. In yet another embodiments, the culturing is performed in vivo. In particular embodiments, the in vivo culturing is performed in a mouse. In certain aspects of the present invention the isolating comprises either or both of protein A affinity and ammonium sulfate precipitation.

Other embodiments of the present invention provide an isolated antibody produced by a process comprising the steps of immunizing a chicken with an antigen composition isolating B cells from the chicken, immortalizing the B cells; selecting an immortalized antibody producing B cell and preparing nucleic acids encoding the antigen binding regions of the light and heavy chain genes thereof; cloning the heavy and light chain antigen binding regions, respectively, into vectors encoding the constant and leader regions of an immunoglobulin heavy chain, the constant and leader regions of an immunogloblin light chain; transferring the vectors into a suitable host cell; culturing the host cell; and isolating the antibody.

Other embodiments provide an isolated antibody that binds immunologically to an antigen selected from the group consisting of CFTR, transforming growth factor beta, lipids, phospholipids, carbohydrates, transcription factors DNA binding molecules; cyclin dependent kinases and RNA binding proteins. In preferred embodiments, the antibody is chimeric. In other embodiments the antibody comprises (i) chicken antibody sequences and (ii) antibody sequences from an animal selected from the group consisting of mouse, rat, rabbit, hamster, horse and human.

The present invention provides a cell that produces antibodies that bind immunologically to an antigen selected from the group consisting of CFTR, transforming growth factor beta, lipids, phospholipids, carbohydrates, transcription factors DNA binding molecules; cyclin dependent kinases and RNA binding proteins. In preferred embodiments, the antibodies are chimeric. In other embodiments, the cell is a myeloma cell. More particularly, the myeloma cell is a mouse myeloma cell. In even more preferred embodiments, the mouse myeloma cell is P3x63.Ag8.653.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The file of this patent contains at least one drawing executed in color. Copies of this patent with color drawings will be provided by the Patent and Trademark Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

The file of this patent contains at least one drawing executed in color. Copies of this patent with color drawings will be provided by the Patent and Trademark Office upon request and payment of the necessary fee.

Figure 1A:
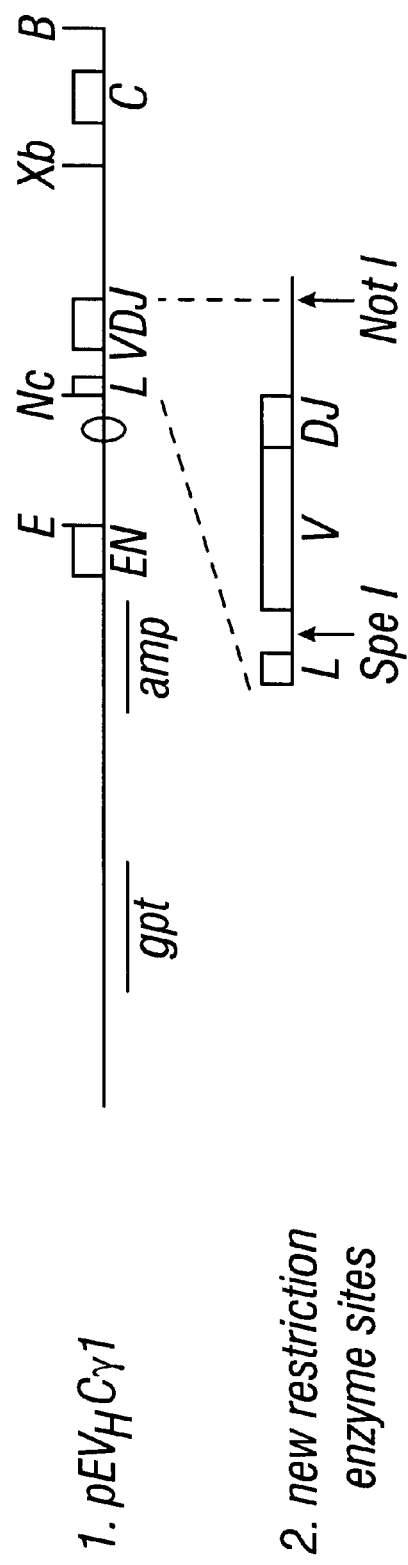

FIG. 1A—Engineering the mutations in the immunoglobulin heavy chain expression vector. Line 1. Diagram of the plasmid $EV_H C_{\gamma l}$. The position of the immunoglobulin heavy chain gene segments of the mouse germline gene 186.2 (Bothwell et al., 198 1) are represented by the open boxes and labeled L (leader), VDJ (rearranged variable, diversity and joining) and C ($C_{\gamma l}$); the line between these boxes represents the intron between these gene segments. 0, represents the immunoglobulin heavy chain promoter, and EN, the heavy chain enhancer; gpt and amp label the position of the selectable markers on the pSV2gpt plasmid which was used to assemble these immunoglobulin gene segments by Simon and Rajewsky (1988). Restriction enzyme sites are indicated: B (Bam HI), E (Eco RI), Nc (Nco I), Xb (Xba I). The arrows indicate the place of insertion of the new restriction enzyme sites, Spe I in the L-V intron and Not I in the J-3' flanking sequences. Line 3. Diagram of the engineered heavy chain expression vector $pEV_H C_{\gamma l}$-SN. Chicken heavy chain PCR primers. Line 4 and 5. Portions of the nucleotide sequence of the chicken immunoglobulin heavy chain gene (Reynaud et al., 1988) L-V intron (SEQ ID NO:24 Ntds 104–364) (line 4) and the J-3' flanking sequences (SEQ ID NO:23 Ntds 152–215) (line 5) showing where the primers, HCSpe and HCNot, will hybridize.

Figure 1:
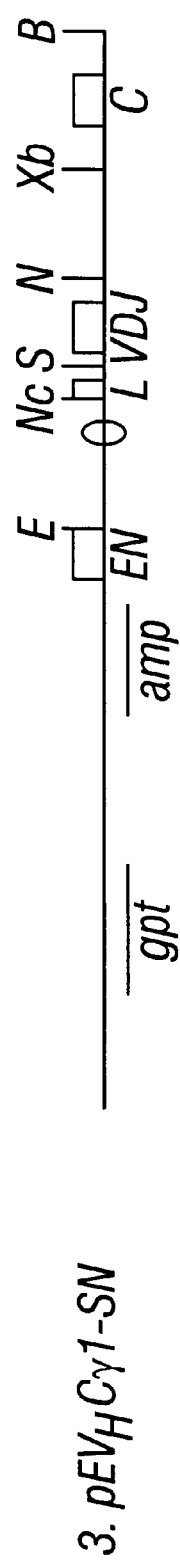
Figure 1B:
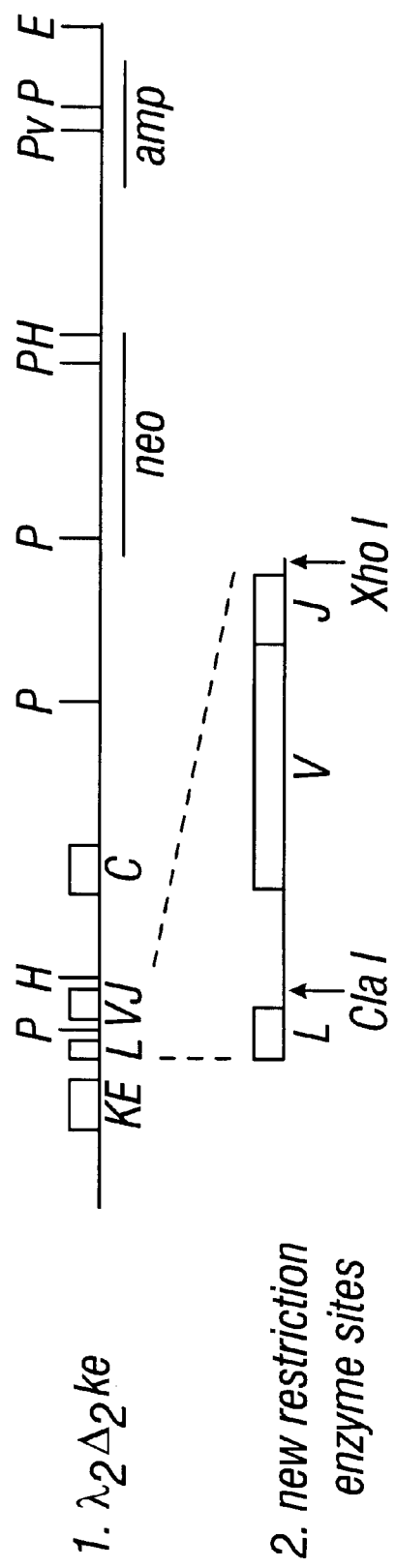
Figure 1:
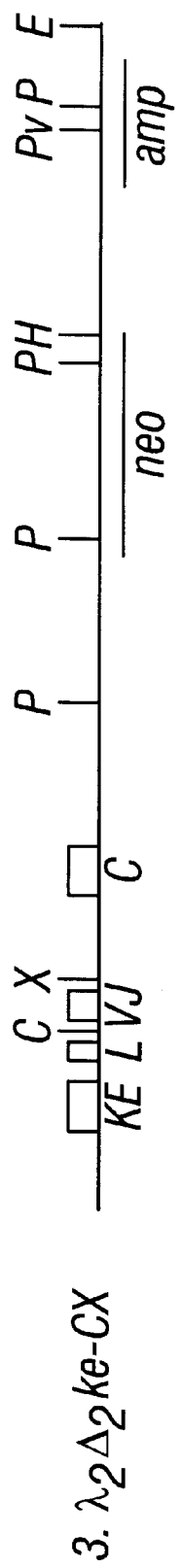

FIG. 1B—Engineering the mutations in the immunoglobulin light chain expression vector. Line 1. Diagram of the $\lambda_2 \delta_2$ke (Alonso et al., 1990). 1. The position of the mouse immunoglobulin λ3 light chain gene segments is indicated by the open boxes, and labeled L (leader), VJ (rearranged variable and joining) and C (λ2 constant). The line between these boxes represents the intron between these gene segments; ke, the light chain enhancer found in the VJ-C intron, and neo and amp the position of the selectable markers. Restriction enzyme sites are: Pv (Pvu I), P (Pst I), H (Hind III), Line 2. The structure of the L and VJ genes are indicated in greater detail. The arrows indicate the positions of the new restriction enzyme sites: Cla I in the L-V intron (SEQ ID NO:21 Ntds 467–660) and Xho I in the VJ-C intron. Line 4. Diagram of the expression vector $\lambda_2 \delta_2$ke-CX (symbols are as for lanes 1 and 2). Chicken light chain PCR primers. Line 4 and 5. Portions of the nucleotide sequence of the chicken immunoglobulin light chain L-V intron (line 4) and the J-3' flanking sequences (SEQ ID NO:21 Ntds 2762–2822) (line 5) showing where the primers LVCla and 839Xho will hybridize.

Figure 2A:
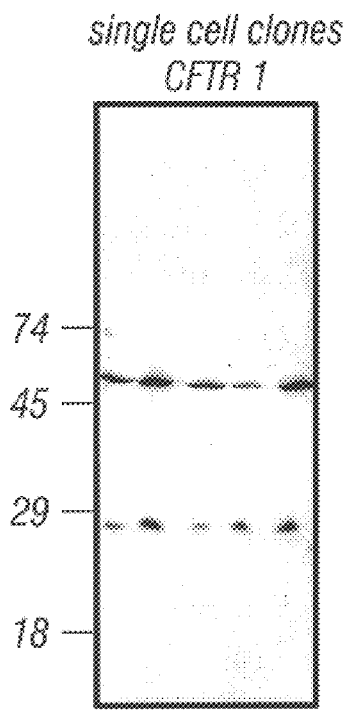

FIG. 2A—Western blot analysis of antibody production. Cytoplasmic proteins, extracted from five CFTR antibody producing cell lines, were separated by electrophoresis on a 10% acrylamide/SDS gel and blotted to nitrocellulose. The blot was probed with HRP-anti-chicken antibody and developed with ECL reagents. Molecular weight markers are indicated in kD.

Figure 2B:
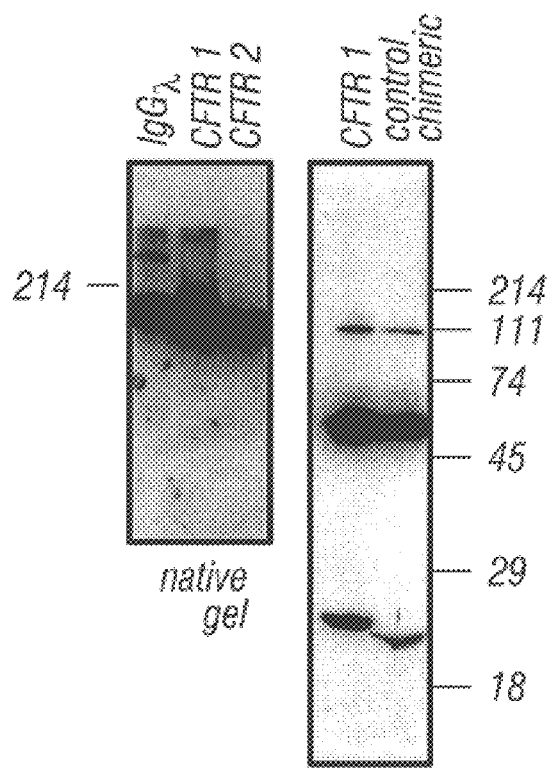

FIG. 2B—Western blot analysis of antibody production. One-half $\mu$g of anti-CFTR antibodies 1, 2 or unknown chimeric antibody, purified by chromatography on Protein A, was analyzed by electrophoresis on a native gel, 10% acrylamide without SDS, or a denaturing gel, 10% acrylamide plus SDS, and transferred to nitrocellulose. The blots were probed with HRP anti-mouse antibody and developed with ECL reagents. One-half µg of purified mouse IgG$_1\lambda$ (PharMingen) was also analyzed on the native gel. Molecular weight markers are indicated in kD.

Figure 3:
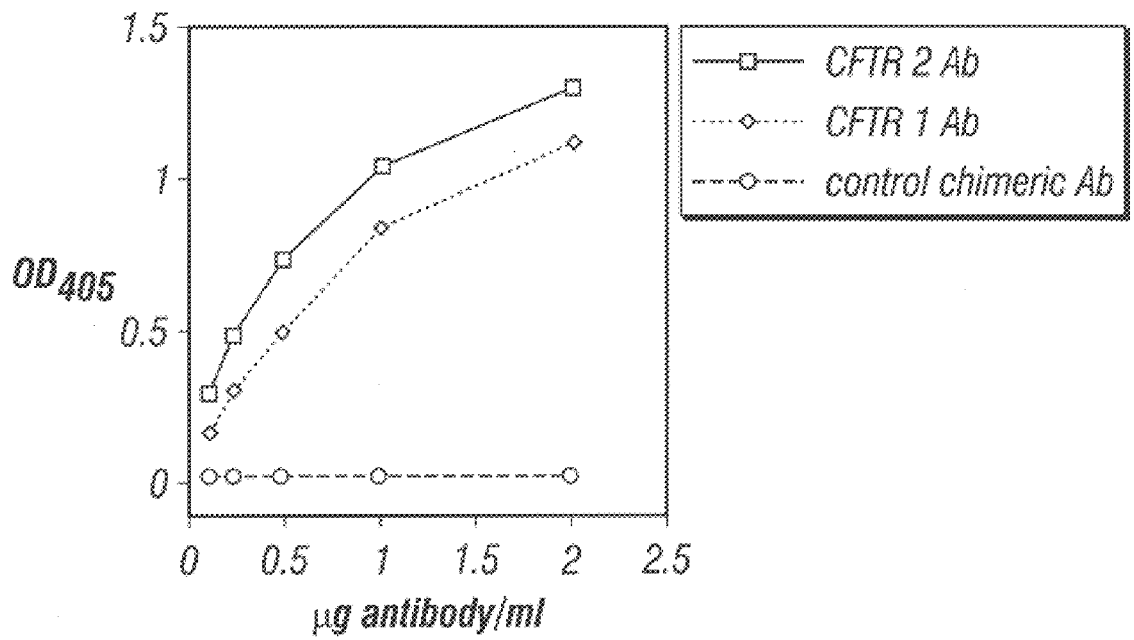

FIG. 3—Graph of an ELISA assay demonstrating the specificity of the CFTR antibodies. A 96-well plate, coated with CFTR-BSA peptide, was incubated with a 2-fold dilution of Protein A purified CFTR antibodies 1 and 2 and a control chicken/mouse chimeric antibody of uncharacterized specificity 8:2, or germline antibodies 16:E5 and 17:E5. Bound antibody was detected with a 1:2000 dilution of AKP-anti chicken IgY. OD$_{405}$ minus the background is plotted versus the calculated concentration of antibody. The values observed for 8:2, 16:E5 and 17:E5 are identical and have been graphed as the single line "control."

FIGS. 4A–D—Immunoperoxidase detection of CFTR in mouse lung. Five micron sections of formalin-fixed mouse lung were stained for CFTR with CFTR antibodies 1 and 2. The presence of bound antibody was detected with biotinylated-anti-mouse antibody and the reagents in a Vectastain ABC Kit. Red color was developed with AEC; counter stain was hematoxylin. Original magnification was 28X. FIG. 4A: A 1:500 dilution of CFTR 1 antibody. FIG. 4B: A 1:50 dilution of CFTR 2 antibody. FIG. 4C: A 1:10 dilution of 8:2, a chimeric antibody of unknown specificity. FIG. 4D: Biotinylated anti-mouse secondary antibody. Long arrows in FIG. 4A and FIG. 4B identify cells stained with CFTR antibodies; the arrow head in FIG. 4D points to the background staining of natural mouse antibodies with the secondary antibody.

DETAILED DESCRIPTION OF THE PREFERRED EMBODIMENTS

I. The Present Invention

In recent years, it has become apparent that the repertoire of potential immune responses in mammalian species is limited. This appears to be due to the failure of mammals to produce antibody to their own proteins, lipids or carbohydrates. As a result, it is difficult to raise monoclonal antibodies in mammals against certain antigenic determinants. Examples of such antigens are the estrogen receptor (Schuh et al., 1992) and the regulatory portions of the cystic fibrosis gene product (Fuller et al., 1992; Denning et al.; 1992;Gregory et al., 1990).

Numerous alternative strategies have been investigated in an effort to develop monoclonal antibodies against some of these "problem" antigens. Phage libraries of recombinant light and heavy chains have been used to generate antibodies specific for conserved antigens, but something on the order of $10^{14}$ phage plaques must be screened to identify a clone with the appropriate specificity. Use of single chain antibodies, designed to minimize the number of clones that must be screened, has been relatively unsuccessful given the low affinity of such antibodies.

Another alternative to raising antibodies in mammals has been the use of chickens. Following immunization, polyclonal antisera can be isolated from chicken egg yolk, about 10% of which is maternal antibody. Investigators have been able to raise polyclonal antisera in chickens against proteins previously shown to be refractory to production of either polyclonal or monoclonal antibodies in mammals. Based on these results, the chicken system appears to be a promising area of research for development of antisera against conserved mammalian antigens.

One of the major goals in chicken-based antibody research has been the development of monoclonal techniques. This has proved problematic, however. In standard mammalian monoclonal techniques, primed B cells are immortalized by fusion with a tumor cell line. The resulting "hybridomas" grow indefinitely in culture and secrete antibody. In the chicken system, there is no satisfactory approach to immortalization of Ig secreting cells. While immortalization of B cells can be achieved, the hybridomas lose the ability to secrete the appropriate antibody within a short time.

The present invention is directed at exploiting the wide range of antibody specificity available in the avian system while, at the same time, overcoming the limitations with the respect to production of monoclonal antibodies. This is accomplished by "rescuing" the variable regions from rearranged Ig genes in chicken B cells. The rescued regions are then inserted into expression cassettes that produce functional Ig light and heavy chains from various species, including humans.

The genomic organization of the chicken heavy and light chain immunoglobulin genes is uniquely suited to the use of genetic techniques in the engineering of antibodies. In the chicken, there is a single V and J region of both the heavy chain (see SEQ ID NO:23, SEQ ID NO:24 and SEQ ID NO:25 and Parvari, et al., 1988) and the light chain (see SEQ ID NO:21 and SEQ ID NO:22 and Parvari, et al., 1989) that is capable of undergoing rearrangement (Reynaud et al, 1985; Weill et al., 1996). Thus, there is a single rearranged locus that contains all the signals and sequences required for producing the antigen binding exons of an immunoglobulin light chain and a single rearranged locus that contains all the sequences necessary to produce the antigen binding exon of an immunoglobulin heavy chain. Diversification occurs by repeated gene conversion events that transfer sequences from numerous pseudogenes to the expressed locus (Thompson et al., 1987; McCormack et al., 1991). Even after diversification (and maturation), the genomic DNA of the expressed locus always has the same L-V intron and the same J-3' flanking sequences. Thus, it is possible to predict, with the absolute certainty, the regions flanking the antigen binding domains of rearranged chicken Ig genes. This makes possible the precise identification of coding sequences that provide antigen specificity and their amplification by the polymerase chain reaction (PCR) using one set of PCR primers for the heavy chain and another pair for the light chain. The respective PCR products can then be cloned into a plasmid expression vector designed to express a complete heavy or light chain molecule when transfected into cells.

In the examples presented below, the inventors describe a system for producing engineered monoclonal antibodies to a conserved mammalian protein. These antibodies have the antigen specificity of antibodies that were derived from an immunized chicken. B cells, harvested from the immunized chicken, were immortalized and the antigen specific immunoglobulin heavy and light chain variable domains amplified by PCR, cloned into modified expression vectors, and expressed following transfection in stable cell lines.

In one such example, a carboxy-terminal peptide from the human cystic fibrosis transmembrane conductance regulator (CFTR) protein, a cAMP activated chloride channel in the cell membrane (Riordan et al., 1989), was employed as an immunogen in chickens. The cellular defect in the disease cystic fibrosis has been mapped to mutations in the CFTR gene (Rich et al., 1990; Cheng et al., 1990; Drumm et al., 1993). Homologues of CFTR have been found in monkey, mouse, rat, cow, monkey, frog and shark; the most highly conserved amino acid residues are in the putative functional domains (Diamond et al., 1991). The carboxy-terminal 13 amino acids are conserved in mouse, rat and cow. To date, no antibody reactive with both the murine and human carboxy terminal domains of CFTR has been reported. As described below, the present inventors were successful in raising antibodies against this antigen in chickens and then transferring portions of the rearranged chicken variable genes into the genetic context of mammalian constant regions. This gene was then transferred to a suitable host cell which produced "chimeric" antibody. The resulting antibodies were reactive with the carboxy terminal domain of both human and mouse CFTR.

The various forms of the present invention, and how it may be fully exploited, are described in detail in the following sections.

II. Antigens and Antigen Preparations For Immunization of Avian Species

The methods for generating monoclonal antibodies (MAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. In the present invention the antibodies are produced in a chicken.

As discussed earlier it is known that certain antigens can not illicit an immune response in mammals due to the presence of certain conserved regions in some proteins. In particular, these conserved regions are not recognized as foreign thus are less immunogenic to closely related species. The present invention provides details of the generation of monoclonal antibodies against such mammalian antigens in an unrelated species such as an avian system. In a preferred embodiment the antibodies are generated in a chicken system. Immunogenic composition of the invention include proteins, carbohydrates lipids, antigen-carrier compositions, derivatives or fragments, thereof. Other exemplary immunogens include but are not limited to transforming growth factor beta, lipids, phospholipids, carbohydrates, transcription factors, DNA binding molecules, cyclin dependent kinases and RNA binding proteins.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund'sadjuvant (a non-specific stimulator of the immune response containing killed *Mycobacteriun tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and titering is repeated until a suitable titer is achieved. When a desired level of immunogenicity is obtained, the immunized animal can be bled and the serum isolated and stored, and/or the animal can be used to generate Mabs.

III. Immunization Protocols for Avian Species

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide or peptide. The immunizing composition is administered in a manner effective to stimulate antibody producing cells. In the present invention chicken are preferred avian species for generation of antibodies however, other avian species such as quails or ducks may also be employed. An appropriate immunization strategy is one that produces a measureable antibody response in the serum and may incorporate any of the routes of injection or adjuvants listed above. In many cases one or more immunizations may be necessary.

IV. Preparation of Immortalized Avian Cells

Following immunization, somatic cells with the potential for producing antibodies, specifically B lymphocytes (B cells), are selected for use in the MAb generating protocol. These cells may be obtained from biopsied spleens, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $1 \times 10^9$ to $10^{10}$ lymphocytes.

The antibody-producing B lymphocytes from the immunized animal are then fused with cells of an immortal B cell, generally one of the same species as the animal that was immunized. B cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of B cell lines may be used, as are known to those of skill in the art (Goding, pp. 65–66, 1986). For example, where the immunized animal is a chicken, one may use either avian leukosis virus transformed B cell lines or real oncogene induced B cell lines.

One preferred B cell line is the R27H4 B cell line, (Nishinaka et al., 1989; 1991) Another B cell line that may be used is the DT40 which is widely available (Baba et al., 1985)

Methods for generating hybrids of antibody-producing spleen or lymph node cells and B cell lines usually comprise mixing somatic cells with the cell line in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding pp. 71–74, 1986).

An alternative method for preparing antibody producing avain cell clones involves transforming a population of antibody producing b cells from a bird with v-rel. Such methods are well known to those of skill in the art and are described in U.S. Pat. Nos. 5,258,299 and 5,049,502 (specifically incorporated herein by reference). These methods generally comprise immunizing a first bird with a desired antigen; separating a population of antibody-producing B-lymphocytes from the first bird and treating the antibody-producing B-lymphocyte population with v-rel under conditions inducing transformation.

To develop antibody-producing clones in vivo, the treated B-lymphocytes are transplanted into a second bird, the second bird having been pretreated to remove normal B-lymphocytes; the transformed B-lymphocytes are allowed to proliferate in the second bird; and then isolated. To develop antibody-producing clones in vitro, the treated B-lymphocytes are not transplanted into a second bird as is done for in vivo preparation of avian cell clones. Instead, the treated B-lymphocytes are incubated under conditions that facilitate proliferation of the antibody-producing clones.

Separation of a population of B-lymphocytes from a bird is preferably from the bursa or spleen, but may also be obtained from bone marrow, gland of Harder, intestinal lining or peripheral blood of the bird. The cells may be separated from other cells and debris by standard density gradient centrifugation, for example, sucrose density gradient. Generally, the majority of antibody-producing B-lymphocytes are IgM+, at least those from the spleen and bursa, but other isotypes may be present, for example, IgG or IgA, depending on the antigen used for the immunization. In order to develop IgG or IgA clones, the separating step could, for example, utilize panning the antibody-producing B-lymphocytes on a solid surface comprising bound antibodies having binding specificity for avian IgM, IgG or IgA.

In a next step after isolation of antibody-producing B-lymphocytes from a live bird, the B-lymphocytes are treated with v-rel under conditions inducing transformation. This may involve transfection with or electroporation-induced entry of an agent containing a v-rel gene. These techniques are well known to those skilled in the art. Agents may include, for example, plasmid vectors comprising cloned v-rel. Also viruses which comprise the v-rel oncogene may be used, for example a reticuloendotheliosis virus or a reticuloendotheliosis virus and a helper virus. In some instances the helper-free reticuloendotheliosis virus is REV-T and the reticuloendotheliosis virus with a helper virus is REV-T(CSV). Other helper viruses may be used, including but not limited to spleen necrosis virus (SNV), attenuated REV-A or duck infectious anemia virus (DIAV). It has been discovered that when a virus is used to infect separated B-cells, either the virus or virus and helper virus may be used for infection. If the infected cells are then to be transferred into a second live bird, any helper virus used must be nontoxic to target cells in the second bird. Thus, REV-A, for example, appears to be directly or indirectly toxic to the target cells of the live animal; however, if the separated B-lymphocytes are transformed and subsequently propagated in vitro, cytotoxicity of the helper virus is not a concern and any suitable helper virus may be used.

After transformation in vitro of isolated B-lymphocytes, the treated B-lymphocytes may either be transferred into a second bird or proliferated in vitro in order to establish antibody producing cell lines.

V. Screening for Antigen Reactivity

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aninopterin or methotrexate is used, the media is supplemented with hypoxanthine and thymidine as a source of nucleotides (HAT medium). Where azaserine is used, the media is supplemented with hypoxanthine.

A preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid. Radioimmunoassays, enzyme immunoassays, cytotoxicity assays, plaque assays, dot immunobinding assays, and the like, may be used.

Any selected hybridomas would then be serially diluted and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

In a preferred embodiment, chicken B cells are immortalized by fusing splenic B cells to R24H4, a hybrid TK-chicken lymphoblastoid cell line (Nishinaka et al., 1989; 1991). These hybridomas can be successfully screened and subcloned; unfortunately stable antibody production is not sustained. However, cells producing antigen-specific antibodies can be identified and the cellular genomic DNA used as the template to amplify the antibody coding sequences by PCR.

VI. Primers and Primer Design

In certain embodiments of the present invention a set of PCR primers is used to amplify heavy and light chain domain gene sequence. The single set of PCR primers and engineered immunoglobulin expression vectors were designed so that the chicken variable domain sequences of a specific antibody could be easily cloned in a plasmid vector that will encode chimeric immunoglobulin which has the variable gene domains of the specific chicken antibody and the leader and constant segments of the mammalian gene sequence. Thus the antibodies produced will have the specificity provided by the chicken variable domain and the accessory functions of the mammalian constant domain.

In order to produce the chimeric immunoglobulins described above it will be necessary to produce specific amplify via PCR primers. Only a single pair is necessary to PCR the chicken immunoglobulin light chain antigen binding exon. The primers are placed in intronic regions that are identical in all functional chicken light chain genes. Only a single primer pair is necessary to amplify via PCR the chicken immunoglobulin heavy chain antigen binding exon. Again the primers are derived from the intronic regions between the leader and variable segments and joining and constant segments. These regions are identical in all functional chicken immunoglobulin heavy chain genes. Ideally, PCR primers contain cloning sites for directional cloning of PCR fragments into immunoglobulin expression constructs. PCR primers should contain at least 15 base pair of sequence from the appropriate L-V intron or antisense J-C intron.

VII. Cloning Vehicles for Immunoglobulin and Cloning Methods

One set of PCR primers is used to amplify the heavy chain antigen binding exon sequences. A second set of PCR primers is used to amplify the light chain antigen binding exon sequences. These PCR products are cloned into the modified expression vectors of the present invention. Each construct will then encode a chimeric immunoglobulin gene that has the antigen binding exon of the specific chicken antibody, and the leader and constant gene segments of the mouse. The antibodies made will thus have antigenic specificity provided by the chicken antigen binding exon and accessory functions provided by the mouse constant domain. In a particular embodiment transfectomas have been made by cotransfecting a heavy and a light chain gene plasmid into the mouse myeloma cell line P3x63.Ag8.653; they are stable and express antibodies that can be purified from the tissue culture supernate. Of course, avian cell lines are also contemplated for use as transfectomas in the present invention. These cell lines are well known to those of skill in the art. These antibodies produced are specific and can be used in standard immunological assays.

The expression vectors used in the present invention had been designed to contain all the signals necessary for immunoglobulin gene transcription in transfected hybridoma cell lines and had been successfully used by others to express full length mouse heavy and light chain immunoglobulin molecules. These vectors were modified in the present invention to permit specific directional cloning of the chicken antigen binding exons. Such modification are well within the skill of the ordinary person in the art.

The heavy chain expression vector, $pEV_H C_{\gamma l}$, contains the rearranged and unspliced mouse heavy chain leader (L), variable (V), diversity (D) and joining (J) gene segments from the germline $V_H$ 186.2 gene (Bothwell et al, 1981) and the $C_{\gamma l}$ constant (C) domain (Honjo et al., 1979); these gene segments, including the natural L-V intron and the J 3'-flanking sequences, had been cloned into pSV2gpt with the heavy chain promoter and enhancer (Simon et al., 1988). In the present example, the heavy chain expression vector was modified by insertional mutagenesis. Nucleotides 12–17 in the mouse L-V intron have been mutated to an SpeI site while a NotI site was introduced into the BamHI site 197 nucleotides 3' of the boundary between the J segment and the J-C intron using an oligonucleotide linker. The resulting cloning vector is designated $pEV_H C_{\gamma l}$-SN.

The light chain expression vector, $p\lambda_2\Delta_2 ke$ (Alonso et al., 1990), contains the mouse κ-chain enhancer, the $\lambda_2$ L and VJ gene segments, and the $C\lambda_2$ constant domain (Wu et al., 1982), cloned into pSV2neo. In the present example the light chain expression construct was modified by cloning an oligonucleotide linker conating a Cle I site into the PstI site at nucleotide 18 in the L-V intron and an oligonucelotide containing an XhoI site into HindIII site 13 nucleotides 3' of the boundary between the J segmant and the JC intron. The resulting cloning vector is designated $p\lambda_2\Delta_2 ke$-CX The essential feature of both of the above cloning vectors is the introduction of unique cloning sites within both the L-V and J-C introns allow directional cloning of the avain antigen binding exons of the immunoglobulin heavy and light chain genes into their respective cloning vectors following PCR with primers containing identical sites. All mammalian immunoglobulin vectors could be similarly modified for the production of chimeric antibodies.

Transfected cells can be selected for the presence of the heavy chain plasmid with HAT and for the light chain plasmid with G418 as described below.

VIII. Template Dependent Amplification Methods

A number of template dependent processes are available to amplify the marker sequences present in a given template sample. These processes include polymerase chain reaction (PCR), reverse transcriptase PCR, ligase chain reaction, isothermal amplification methods, strand displacement amplification among others and are discussed in further detail below.

1. Polymerase Chain Reaction

One of the best known amplification methods is the polymerase chain reaction (referred to as PCR) which is described in detail in U.S. Pat. Nos. 4,683,195, 4,683,202 and 4,800,159, and in Innis et al., 1990, each of which is incorporated herein by reference in its entirety.

A number of template dependent processes are available to amplify the marker sequences present in a given template sample. One of the best known amplification methods is the polymerase chain reaction (referred to as PCR) which is described in detail in U.S. Pat. Nos. 4,683,195, 4,683,202 and 4,800,159, and in Innis et al., 1990, each of which is incorporated herein by reference in its entirety.

Briefly, in PCR, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

In PCR, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR amplification is directly proportional to the starting concentration of the target before the reaction began. By determining the concentration of the amplified products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR products and the relative mRNA abundances is only true in the linear range of the PCR reaction. Thus conditions for PCR must be optimized to ensure that the reaction is being performed in the linear range, however, such manipulations are well within the skill of the ordinary person in the art.

2. Other Template Dependent Amplification Methods

A reverse transcriptase PCR amplification procedure may be performed in order to quantify the amount of mRNA amplified. In such a procedure, reverse transcription (RT) of RNA to cDNA is followed by relative quantitative PCR (RT-PCR) of specific mRNA species in a particular sample. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

Another method for amplification is the ligase chain reaction ("LCR"), disclosed in EPO No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention, Walker et al., (1992).

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989; Gingeras et al., PCT Application WO 88110315, incorporated herein by reference in their entirety). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Davey et al., EPO No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, M. A., In: *PCR PROTOCOLS: A GUIDE TO METHODS AND APPLICATIONS*, Academic Press, N.Y., 1990; Ohara et al., 1989; each herein incorporated by reference in their entirety).

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu et al., (1989), incorporated herein by reference in its entirety.

IX. Transformation of Host Cells With Cloned Immunoglobulin Genes

1. Genetic Constructs

Within certain embodiments expression vectors are employed to express various genes to encode a chimeric immunoglobulin that has the variable gene domains of the specific chicken antibody, which can then be purified and, be used to generate antisera or monoclonal antibody with which further studies may be conducted. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the antigenic products are also provided, as is an element that links expression of the drug selection markers to expression of the polypeptide.

(i) Regulatory Elements

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

In preferred embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies amongst others, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of direction the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product. Tables 2 and 3 list several elements/promoters which may be employed, in the context of the present invention, to regulate the expression of the gene of interest. This list is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene of interest in an expression construct (Table 1 and Table 2). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 1

ENHANCER/PROMOTER

Immunoglobulin Heavy Chain
Immunoglobulin Light Chain
T-Cell Receptor
HLA DQ α and DQ β
β-Interferon
Interleukin-2
Interleukin-2 Receptor
MHC Class II 5
MHC Class II HLA-DRα
β-Actin
Muscle Creatine Kinase
Prealbumin (Transthyretin)
Elastase I
Metallothionein
Collagenase
Albumin Gene
α-Fetoprotein
τ-Globin
β-Globin
e-fos
c-HA-ras
Insulin
Neural Cell Adhesion Molecule (NCAM)
α1-Antitrypsin
H2B (TH2B) Histone
Mouse or Type I Collagen
Glucose-Regulated Proteins (GRP94 and GRP78)
Rat Growth Hormone
Human Serum Amyloid A (SAA)
Troponin I (TN I)
Platelet-Derived Growth Factor
Duchenne Muscular Dystrophy
SV40
Polyoma
Retroviruses
Papilloma Virus
Hepatitis B Virus
Human Immunodeficiency Virus
Cytomegalovirus
Gibbon Ape Leukemia Virus

TABLE 2

| Element | Inducer |
| --- | --- |
| MT II | Phorbol Ester (TPA) |
| | Heavy metals |
| MMTV (mouse mammary tumor virus) | Glucocorticoids |

TABLE 2-continued

| Element | Inducer |
| --- | --- |
| β-Interferon | poly(rI)X |
| | poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyroid Hormone |
| Insulin E Box | Glucose |

In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

(ii) Selectable Markers

In certain embodiments of the invention, the cells contain nucleic acid constructs of the present invention, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

(iii) Multigene constructs and IRES

In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

2. Delivery of Genetic Constructs

There are a number of in vivo and in vitro methods by which nucleic acids may introduced into cells. Several such methods, including viral and non-viral transduction methods, are outlined below. In vivo delivery may be achieved using an adenovirus expression vector (Grunhaus and Horwitz, 1992; Renan 1990; Graham and Prevec, 1991), retroviruses (Coffin, 1990; Roux et al., 1989), as well as other viral vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpes viruses may be employed. These viral vectors offer several attractive features for various mammalian cells (Ridgeway, 1988; Baichwal and Sugden, 1986; Coupar et al., 1988; Horwich et al., 1990).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In one embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al., (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

Primary animal cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question. The immortalization of cells for the production of proteins is discussed in further detail elsewhere in the specification.

X. Uses for Monoclonal Antibodies

1. Immunodetection Methods

In certain embodiments, the present invention concerns immunodetection methods for binding, purifying, removing, quantifying or otherwise generally detecting biological components. The antibodies prepared in accordance with the present invention, may be employed to detect the encoded proteins or peptides. The steps of various useful immunodetection methods have been described in the scientific literature, such as, e.g., Nakamura et al. (1987).

In general, the immunobinding methods include obtaining a sample suspected of containing a protein, peptide or antibody, and contacting the sample with an antibody or protein or peptide in accordance with the present invention, as the case may be, under conditions effective to allow the formation of immunocomplexes.

The immunobinding methods include methods for detecting or quantifying the amount of a reactive component in a sample, which methods require the detection or quantitation of any immune complexes formed during the binding process. Here, one would obtain a sample suspected of containing an antigen and contact the sample with an antibody or encoded protein or peptide prepared by the present invention, as the case may be, and then detect or quantify the amount of immune complexes formed under the specific conditions.

In terms of antigen detection, the biological sample analyzed may be any sample that is suspected of containing a particular antigen of interest, such as a pancreatic β-cell, a homogenized tissue extract, an isolated cell, a cell membrane preparation, separated or purified forms of any of the above protein-containing compositions, or even any biological fluid that comes into contact with diabetic tissue, including blood.

Contacting the chosen biological sample with the antibody under conditions effective and for a period of time sufficient to allow the formation of immune complexes (primary immune complexes) is generally a matter of simply adding the composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. Patents concerning the use of such labels include U.S. Pat. Nos. 3,817,837;

3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The antibody employed in the detection may itself be linked to a detectable label, wherein one would then simply detect this label, thereby allowing the amount of the primary immune complexes in the composition to be determined.

Alternatively, the first added component that becomes bound within the primary immune complexes may be detected by means of a second binding ligand that has binding affinity for the encoded protein, peptide or corresponding antibody. In these cases, the second binding licand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the encoded protein, peptide or corresponding antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if desired.

2. Immunohistochemistry

The antibodies of the present invention may also be used in conjunction with both fresh-frozen and formalin-fixed, paraffin-embedded tissue blocks prepared for study by immunohistochemistry (IHC). For example, each tissue block consists of 50 mg of residual "pulverized" diabetic tissue. The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" diabetic tissue at room temperature in phosphate buffered saline (PBS) in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25–50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

3. ELISA

As noted, it is contemplated that the antibodies of the present invention will find utility in immunohistochemistry and in ELISA assays. One evident utility of the encoded antigens and corresponding antibodies is in immunoassays for the detection of a particular antigen for daignostic and quantitative purposes.

Immunoassays, in their most simple and direct sense, are binding assays. Certain preferred immunoassays are the various types of enzyme linked immunosorbent assays (ELISA) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, antibodies binding to the encoded proteins of the invention are immobilized onto a selected surface exhibiting protein affinity, such as a well in a polystyrene microtiter plate. Then, a test composition suspected of containing the particular antigen of interest, such as a clinical sample, is added to the wells. After binding and washing to remove non-specifically bound immune complexes, the bound antibody may be detected. Detection is generally achieved by the addition of a second antibody specific for the target protein, that is linked to a detectable label. This type of ELISA is a simple "sandwich ELISA". Detection may also be achieved by the addition of a second antibody, followed by the addition of a third antibody that has binding affinity for the second antibody, with the third antibody being linked to a detectable label.

In another exemplary ELISA, the samples suspected of containing a particular antigen are immobilized onto the well surface and then contacted with the antibodies of the invention. After binding and washing to remove non-specifically bound immune complexes, the bound antigen is detected. Where the initial antibodies are linked to a detectable label, the immune complexes may be detected directly. Again, the immune complexes may be detected using a second antibody that has binding affinity for the first antibody, with the second antibody being linked to a detectable label.

Another ELISA in which the proteins or peptides are immobilized, involves the use of antibody competition in the detection. In this ELISA, labeled antibodies are added to the wells, allowed to bind to the antigen, and detected by means of their label. The amount of marker antigen in an unknown sample is then determined by mixing the sample with the labeled antibodies before or during incubation with coated wells. The presence of marker antigen in the sample acts to reduce the amount of antibody available for binding to the well and thus reduces the ultimate signal. This is appropriate for detecting antibodies in an unknown sample, where the unlabeled antibodies bind to the antigen-coated wells and also reduces the amount of antigen available to bind the labeled antibodies.

Irrespective of the format employed, ELISAs have certain features in common, such as coating, incubating or binding, washing to remove non-specifically bound species, and detecting the bound immune complexes. These are described as follows:

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating of nonspecific adsorption sites on the immobilizing surface reduces the background caused by nonspecific binding of antisera to the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin (BGG) and phosphate buffered saline (PBS)/Tween™. These added agents also tend to assist in the reduction of nonspecific background.

The "suitable" conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C. or so.

Following all incubation steps in an ELISA, the contacted surface is washed so as to remove non-complexed material. A preferred washing procedure includes washing with a solution such as PBS/Tween™, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this label will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween™).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation is then achieved by measuring the degree of color generation, e.g., using a visible spectra spectrophotometer.

4. Use of Antibodies for Radioimaging

The antibodies of this invention can be used to quantify and localize the expression of the encoded marker proteins. The antibody, for example, will be labeled by any one of a variety of methods and used to visualize the localized concentration of the cells producing the encoded protein. Such an assay also will reveal the subcellular localization of the antigen, which can have diagnostic and therapeutic applications.

In accordance with this invention, the monoclonal antibody or fragment thereof may be labeled by any of several techniques known to the art. The methods of the present invention may also use paramagnetic isotopes for purposes of in vivo detection. Elements particularly useful in Magnetic Resonance Imaging ("MRI") include $^{157}$Gd, $^{55}$Mn, $^{162}$Dy, $^{52}$Cr, and $^{56}$Fe.

Administration of the labeled antibody may be local or systemic and accomplished intravenously, intraarterially, via the spinal fluid or the like. Administration may also be intradermal or intracavitary, depending upon the body site under examination. After a sufficient time has lapsed for the monoclonal antibody or fragment thereof to bind with the diseased tissue, for example 30 minutes to 48 hours, the area of the subject under investigation is examined by routine imaging techniques such as MRI, SPECT, planar scintillation imaging or newly emerging imaging techniques. The exact protocol will necessarily vary depending upon factors specific to the patient, as noted above, and depending upon the body site under examination, method of administration and type of label used; the determination of specific procedures would be routine to the skilled artisan. The distribution of the bound radioactive isotope and its increase or decrease with time is then monitored and recorded. By comparing the results with data obtained from studies of clinically normal individuals, the presence and extent of the diseased tissue can be determined.

It will be apparent to those of skill in the art that a similar approach may be used to radio-image the production of the antigenic proteins in human patients. The present invention provides methods for the in vivo diagnosis of disease in a patient. Such methods generally comprise administering to a patient an effective amount of an antigen specific antibody, to which antibody is conjugated a marker, such as a radioactive isotope or a spin-labeled molecule, that is detectable by non-invasive methods. The antibody-marker conjugate is allowed sufficient time to come into contact with reactive antigens that are present within the tissues of the patient, and the patient is then exposed to a detection device to identify the detectable marker.

5. Pharmaceutical compositions

The present invention is also contemplated to provide antibodies for the treatment of diseases associated with antigens that are not recognized by the animal in which they are presented. In one example the present invention provides antibodies against CFTR for the treatment of cystic fibrosis. Passive immunity may aid in the treatment of such diseases, and such treatments are contemplated by the present invention.

Passive immunity is defined, for the purposes of this application, as the transfer to an organism of an immune response effector that was generated in another organism. The classic example of establishing passive immunity is to transfer antibodies produced in one organism into a second, immunologically compatible animal. The present invention contemplates both of these approaches.

Antibodies, antisera and immune effector cells are raised using the methods of the present invention as discussed above. The primary animal is vaccinated with the immunogen according to the present invention, with or without an adjuvant, to generate an immune response. The immune response may be monitored, for example, by measurement of the levels of antibodies produced, using standard ELISA methods.

Antibodies, antisera or immune effector cells, prepared as set forth above, are injected into hosts to provide passive immunity against the disease to be treated. For example, an antibody composition is prepared by mixing, preferably homogeneously mixing, at least one antibody with at least one pharmaceutically or veterinarally acceptable carrier, diluent, or excipient using standard methods of pharmaceutical or veterinary preparation. The amount of antibody required to produce a single dosage form will vary depending upon the disease being vaccinated against, the individual to be treated and the particular mode of administration. The specific dose level for any particular individual will depend upon a variety of factors including the age, body weight, general health, sex, and diet of the individual, time of administration, route of administration, rate of excretion, drug combination and the severity of the disease.

The antibody composition may be administered intravenously, subcutaneously, intranasally, orally, intramuscularly, vaginally, rectally, topically or via any other desired route. Repeated dosings may be necessary and will vary, for example, depending on the clinical setting, the particular disease, the condition of the patient and the use of other therapies.

Where clinical applications are contemplated, it will be necessary to prepare such pharmaceutical compositions of antibodies in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the compositions of the present invention, its use in therapeutic compositions is contemplated. Supplementary active ingredients also can be incorporated into the compositions.

The monoclonal antibodies of the present invention may include classic pharmaceutical preparations. Administration of these compositions according to the present invention may be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the antibodies of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell'sSolution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example. hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

6. Kits

In still further embodiments, the present invention concerns immunodetection kits for use with the immunodetection methods described above. As the encoded proteins or peptides may be employed to detect antibodies and the corresponding antibodies may be employed to detect encoded proteins or peptides, either or both of such components may be provided in the kit. The immunodetection kits will thus comprise, in suitable container means, an encoded protein or peptide, or a first antibody that binds to an encoded protein or peptide, and an immunodetection reagent.

In certain embodiments, the encoded protein or peptide, or the first antibody that binds to the encoded protein or peptide, may be bound to a solid support, such as a column matrix or well of a microtiter plate.

The immunodetection reagents of the kit may take any one of a variety of forms, including those detectable labels that are associated with or linked to the given antibody or antigen, and detectable labels that are associated with or attached to a secondary binding ligand. Exemplary secondary ligands are those secondary antibodies that have binding affinity for the first antibody or antigen, and secondary antibodies that have binding affinity for a human antibody.

Further suitable immunodetection reagents for use in the present kits include the two-component reagent that comprises a secondary antibody that has binding affinity for the first antibody or antigen, along with a third antibody that has binding affinity for the second antibody, the third antibody being linked to a detectable label.

The kits may further comprise a suitably aliquoted composition of the encoded protein or polypeptide antigen, whether labeled or unlabeled, as may be used to prepare a standard curve for a detection assay.

The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody or antigen may be placed, and preferably, suitably aliquoted. Where a second or third binding ligand or additional component is provided, the kit will also generally contain a second, third or other additional container into which this ligand or component may be placed. The kits of the present invention will also typically include a means for containing the antibody, antigen, and any other reagent containers in close confinement for commercial sale. Such containers may include injection or blow-molded plastic containers into which the desired vials are retained.

XII. Examples

The following examples are included to demonstrate preferred embodiments of the present invention. It should be appreciated by those of skill in the art that that techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar results without departing from the spirit and scope of the invention.

Example 1: Materials and Methods

Immunization. An adult female White Leghorn line SC chicken (Hyline Farms, Callas Center, Iowa), approximately two months of age, was immunized with a peptide-carrier complex containing the 13 amino acid sequence at the carboxy-terminus of the human cystic fibrosis transmembrane conductance regulator (CFTR) protein coupled to keyhole limpet hemocyanin (KLH). Approximately 400 $\mu$g of the peptide-carrier complex, emulsified in complete Freund's adjuvant, was administered subcutaneously into two sites over the rib cage. Twelve days after the first immunization, the chicken was given an intravenous boost of 100 $\mu$g of antigen in saline. On day 13, the animal was sacrificed by $CO_2$ inhalation and the spleen extracted for lymphocyte preparation.

Fusion. Lymphocytes were extracted from the spleen by teasing and separated from red blood cells by centrifugation on Ficoll-Hypaque gradients. The cells were washed twice in RPMI 1640 (Gibco BRL) and fused with the rel immortalized chicken B-cell line R27H4, using standard cell fusion methodology. In brief, $1\times10^8$ R27H4 cells were washed twice in RPMI, combined with an equal number of lymphocytes and pelleted by centrifugation. Approximately 0.5 ml of 40% PEG solution was added to the dry pellet and mixed by gentle agitation. After one minute, the PEG was diluted up by the slow, dropwise addition of 50 ml of RPMI. Cells were then pelleted by centrifugation and resuspended in plating medium (50% HAMS F10, 50% RPMI, 10% FBS, 10% chicken serum, 10% DT40 conditioned medium (), 1X HAT, $5\times10^{-5}$M $\beta$-mercaptoethanol, penicillin/streptomycin, 1-glutamine, fungizone and gentarnycin) at a density of $3\times10^6$ spleen cells per ml. The fusion mixture was plated in 24 well plates, 1 ml/well, a total of 15 plates. Fusion wells were fed on days 7, 10, 14 and 16 by aspiration of half of the media and replacement with fresh media. Eighteen to twenty days after fusion, supernates from positive wells were screened for the presence of peptide-specific antibodies by ELISA. Positive wells were expanded and frozen after a limited number of passages.

Preparation of genomic DNA. Genomic DNA was made from cell lines, defrosted and grown for two passages in RPMI-10% FBS. Approximately $2\times10^7$ cells were harvested by centrifugation, washed twice in cold PBS (Gibco), once in RSB (10 mM Tris pH 7.4, 10 mM NaCl, 5 MM $MgCl_2$), and lysed in 0.5% NP40-RSB. The nuclei were pelleted by centrifugation, resuspended in RSB and lysed by the addition of 2X SDS (1% SDS, 20 mM Tris pH 7.4, 60 mM NaCl, 10 mM EDTA) at 65° C. DNA was purified, following digestion with 200 $\mu$g/ml of Proteinase K, by precipitation in 3M NH$_4$ Acetate150% isopropanol. The DNA pellet was washed twice in 70% ethanol/50 mM NaCl and resuspended in TE (10 mM Tris pH 7.2, 1 mM EDTA).

Constructing the heavy chain expression vector. Plasmids pEV$_H$C$_{\gamma l}$. (Simon and Rajewsky, 1988) was used to construct the heavy chain expression vector pEV$_H$C$_{\gamma l}$-SN. Two new restriction enzyme sites were engineered in pEV$_H$C$_{\gamma l}$, using standard techniques of molecular mutagenesis and cloning. A Not I site was created in the J 3'-flanking region by cloning into the BamHI site, 197 nucleotides (n) from J, the double-stranded linker that encodes a Not I site flanked by BamHI sequences; this linker was made by self annealing the oligonucleotide GATCCGCGGCCGCG (SEQ ID NO: 1). A Spe I site was created in the L-V intron by two step PCR mutagenesis. PRC primers AAGGGGCTCACACTAGTAGGCTTGAGG (SEQ ID NO:2) and

CCTCAAGCCACTAGTGTGAGCCCCTT (SEQ ID NO:3)

used with primers outside of the LVDJ sequence, 5' at the Nco I site, and 3' at the engineered Not I site, generated a new 700 bp Nco I/Not I fragment which, when cloned into pEV$_H$C$_{\gamma l}$-N, replaced the sequences at nucleotides 12–17 in the mouse L-V intron with an Spe I site, (plasmid LVDJ-SN). The plasmid pEV$_H$C$_{\gamma l}$-SN was made by cloning the 3.8 kb EcoRI/Xba I fragment from LVDJ-SN in place of the corresponding EcoRI/Xba I fragment of pEV$_H$C$_{\gamma l}$.

Constructing the light chain expression vector. Plasmid λ$_2$Δ$_2$ke (Alonso et al., 1990) was used to construct the light chain expression vector λ$_2$Δ$_x$ke-CX. Two new restriction enzyme sites were engineered. A Xho I site was created by cloning into the Hind III site, 3' of the rearranged VJ gene segment, the double-stranded linker that encodes a Xho I site flanked by Hind III sequences; this linker was made by self annealing the oligonucleotide AGCTTGCTCGAGCA (SEQ ID NO:4). A Cla I site was created by cloning into the Pst I site in the L-V intron the double-stranded oligonucleotide formed by annealing GTGGGTATCGATTGGCTGATATCCTGCA (SEQ ID NO:5), and

GGATATCAGCCAATCGATACCCACTGCA (SEQ ID NO:6),

Standard cloning procedures were used. All plasmids were grown in the bacterial strain DH5α. DNA was prepared by alkaline lysis and purified by banding in CsCl gradients. The HinD III and Pst I partial digestions of λ$_2$Δ$_2$ke and of λ$_2$Δ$_2$ke-X respectively were performed by two-fold serial dilution of the restriction enzyme digest so that a linear product was made in two or more of the dilutions; it was purified by agarose gel electrophoresis and electroelution from the gel slice. Oligonucleotides were synthesized by Operon Technologies or the HHMI Oligonucleotide Synthesis Facility at the University of Chicago. Double-stranded linkers were made by incubating 2 nmole of the oligonucleotide(s) in 10 mM Tris pH 7.2, 100 mM NaCl, 0.1 mM EDTA at 65° C. with slow cool to room temperature. Correct position and sequence of the new restriction sites was confirmed by dideoxy-chain termination DNA sequencing with Sequenase (U.S. Biochemical Corp.).

PCR and cloning the chicken VJ and VDJ gene segments. The VDJ sequences of the chicken immunoglobulin heavy chain gene were synthesized by PCR using the oligonucleotide primers HCSpe:

(5'GGACTAGTGTCAACGGGGGGTCTCACGGGGG-GCCGGCTC (SEQ ID NO:7) and HCNot:

(5' ATAAGAATGCGGCCGCGGCAATTTT-GGGGGGGGTTGAAGACT (SEQ ID NO:8) (HHMI Oligonucleotide Synthesis Facility, University of Chicago). These oligonucleotides will hybridize to nucleotides 101–131 in the chicken L-V intron and nucleotides 5–35 in the sequences 3' of the VDJ gene respectively (FIG. 1A). The VJ sequences of the chicken immunoglobulin light chain gene (SEQ ID NO:1) were synthesized by PCR using the oligonucleotide primers LVCla:

(5° CCATCGATGACTGTGGGCACGGGGCTCT-GTCCCATTGCTGC 3'; SEQ ID NO:9) and 839Xho (5° CCGCTCGAGGGAAGAAAGACCGAGAC-GAGGTCAGCGACT 3' SEQ ID NO:10) (Operon Technologies). These oligonucleotides will hybridize to nucleotides 23–55 in the chicken light chain L-V intron and nucleotides 5–34 in the intron 3' of the VJ gene sequences respectively (FIG. 1B). Approximately 100 ng of genomic DNA, 100 pmoles of each PCR primer, dXTP, 10X buffer and 0.5 μl cloned pfu polymerase (Stratagene) were assembled and the PCR performed at 94° C. 1 min. 30 sec., 65° C. 1 min., 72° C. 4 min. for 30–35 cycles (Perkins-Elmer Gene Amp PCR System 9600). The 530 bp heavy chain and the 500 bp light chain product were purified by electrophoresis in a 1% agarose gel, and recovered from the gel by electroelution. The heavy chain product was digested with Spe I and Not I and cloned into Spe I/Not I digested pEV$_H$C$_{\gamma l}$-SN. The light chain product was digested with Cla I and Xho I and cloned into Cla I/Xho I digested λ$_2$Δ$_2$ke-CX. The sequence of the light chain VJ and the heavy chain VDJ regions were determined by dideoxy chain-termination sequencing with Sequenase.

Transfection, selection and maintenance of transfectomas. Transfectomas were made in the non-secreting murine myeloma cell line P3x63.Ag8.653 (ATCC No. CRL-1580). 5×10$^6$ cells were harvested from a stock culture split to 2×10$^5$ cells/ml 24 hours prior to use, resuspended in 0.8 ml RPMI, and cotransfected with 1 μg light chain plasmid and 7.5 μg heavy chain plasmid, each linearized with Pvu I. Transfection was by electroporation (BioRad Gene Pulser Transfection Apparatus) at 960 μF and 0.3 kV. Following transfection, cells were held on ice for 10 min., then plated and grown in 10 mls RPMI-10% FBS (supplemented with L-glutamine, penicillin/streptomycin, non-essential amino acids, and β-mercaptoethanol) for 48 hours. Cells were selected in medium containing 1.0 mg/ml G4 18 either as a bulk culture or plated in six 96-well plates per transfection. Following selection, cultures were assayed for immunoglobulin production by testing tissue culture supernates and cytoplasmic extracts by ELISA or western blot. Positive cultures or single cell clones were identified, and expanded. Cultures were maintained in RPMI-10% FBS +1.0 mg/ml G418 and split biweekly at approximately 1×10$^5$ cells/ml.

Tissue culture supernates and antibody purification. Tissue culture supernates were harvested from stock cultures at day 4+ by centrifugation to pellet the cells; the supernate was removed filtered through a 0.2 μm filter or transferred to a clean tube and stored at 4° C. Cytoplasmic extracts were prepared from the resuspended cell pellet by lysis in 0.2% NP40. Nuclei were removed by centrifugation and the cytoplasmic extract supernate stored at −20° C. Antibody was purified from tissue culture supernates by column chromatography on Protein A (Pierce Immunopure IgG (Protein A) Purification Kit) or Protein G (Boehringher-Mannheim) according to the manufacturer's protocol, concentrated by incubation with PEG-8000, dialysed into PBS and stored at 4° C. Protein concentration was determined (BioRad Protein Assay Reagen) with BSA as the standard, or by the formular OD280/1.44=mg Ab/ml.

ELISA. 96 well plates (Nunc ImmunoPlate MaxiSorb) were coated with 20 µg protein/ml of a peptide conjugate CFTR-BSA (Research Genetics), CFTR-KLH or CSD.2-KLH (Duckett et al., 1996) in BBS (borate buffered saline, pH 8.8) or 2 µg/ml of rat anti-mouse $IgG_1$ (PharMingen 02001D) in BBS, 100 µl/well, at room temperature (RT) for at least 3 hours, washed in 0.05% TritonX-100 in PBS, and blocked with 1% BSA in PBS (BSAIPBS), 200 µl/well. Tissue culture supernate or purified antibody prepared in BSA/PBS or RPMI was added, 100 µl/well, and incubated at RT for 90–180 min. The plates were washed, and then incubated with alkaline-phosphatase (AKP) conjugated rat anti-mouse λ1+2 (PharMingen 02173E), AKP-rabbit anti-chicken IgY (Jackson ImmunoResearch Laboratories), or AKP-goat anti-mouse IgG+IgM (H+L) diluted 1:2000 in BSA/PBS for 90' at RT. The plates were developed with 1.0 mg/ml p-nitrophenyl phosphate (Sigma 104 Phosphate Substrate Tablets) in diethanolamine/$MgCl_2$ buffer pH 9.8. The $OD_{405}$ was read (Spectra Max 250, Coulter Electronics using SoftMax for Macintosh). In some experiments, purified mouse $IgG_1$ λ (PharMingen 0301 ID) was used to generate a standard curve.

Protein gels and Western blots. For denaturing gel electrophoresis, polyacrylamide gels were prepared. Samples were prepared in solubilization buffer and heated in a 100° C. heating block for 5–10' prior to electrophoresis. For native gel electrophoresis, polyacrylamide gels were prepared excluding SDS from the gel components. Samples were prepared in solubilization buffer without SDS and β-mercaptoethanol and not heated prior to loading on the gel; the running buffer lacked SDS. Following electrophoresis, gels were transferred electrophoretically to nitrocellulose (BioRad Trans-Blot) at 150 mA for 3 hours. The Western blot analysis was done by blocking the nitrocellulose with 5% skim milk-TBS-T (40 mM Tris pH 7.4, 100 mM NaCl, 0.02% Tween-20); the blots were then incubated with horseradish peroxidase (HRP) rabbit anti-chicken IgY (Jackson Laboratories) or HRP-goat anti-mouse IgG+IgM (H+L) (Pierce), and developed using ECL reagents (Amersham).

Immunocytochemistry. Five micron sections of mouse lung, formalin fixed and embedded in paraffin, were deparaffinized in xylene, hydrated in a graded alcohol series (100%, 95%, PBS) and the antigen retrieved by heating in 10 mM citrate buffer pH 6.0 in a pressure cooker for one minute past the time the pressure valve was extended. The sections were incubated with the experimental and control antibodies diluted in 0.1% BSA in PBS for 45 min. at RT, and then washed briefly in PBS. Incubation with biotinylated anti-mouse IgG (Vectastain Elite ABC Kit), and ABC reagent were performed according to the manufacturer's protocol. (Vector Laboratories). The slides were developed by the addition of 3-amino-9-ethyl carbazone (AEC) (Sigma) in N-N-dimethylformramide and $H_2O_2$; the counterstain was hematoxylin.

Example 2: Results

The objective of this study was to make chicken monoclonal antibodies. Standard hybridoma and transfectoma techniques were used with additional steps designed specifically for the chicken. In particular, a single set of PCR primers and engineered immunoglobulin expression vectors were designed so that the chicken variable domain sequences encoding a specific antibody could be easily cloned and expressed. In the experiments reported here, chimeric chicken/mouse antibodies to the cystic fibrosis transmembrane conductance regulator (CFTR) protein were made. In brief, B cells harvested from the spleen of the immunized chicken are immortalized by fusion to R27H4, a hybrid chicken B cell lymphoblastoid cell line, using standard hybridoma techniques. Following selection and screening, the DNA from cells making antigen-specific antibodies is used as the template in polymerase chain reactions to amplify the expressed antibody genes. These heavy chain and light chain PCR products are then cloned into the immunoglobulin expression vectors to produce a gene encoding a chimeric molecule with the chicken antigen-specific variable domain sequences and mouse leader and constant domain sequences. Transfectomas are made by cotransfecting a pair of heavy chain and light chain expression vectors into the mouse myeloma cell line P3x63.Ag8.653. The CFTR antibodies, made from the transfected heavy and light chain molecules, are secreted into the culture medium and are easily harvested and purified.

Vector design and modification. The expression vectors that were modified had been designed to contain all the signals necessary for immunoglobulin gene transcription in transfected hybridoma cell lines and had been successfully used by others to express full length mouse heavy and light chain immunoglobulin molecules. The heavy chain expression vector, $pEV_HC_{\gamma l}$, contains the rearranged and unspliced mouse heavy chain leader (L), variable (V), diversity (D) and joining (J) gene segments from the germline $V_H$ 186.2 gene (Bothwell et al., 1981) and the $C_{\gamma l}$ constant (C) domain (Honjo et al., 1979); these gene segments, including the natural L-V intron and the J 3'-flanking sequences, had been cloned into pSV2gpt with the heavy chain promoter and enhancer (Simon et al., 1988). The light chain expression vector, $p\lambda_2\Delta_2ke$ (Alonso et al., 1990) contains the mouse K-chain enhancer, the $\lambda_2$ L and VJ gene segments, and the $C\lambda_2$ constant domain (Wu et al., 1982) cloned into pSV2neo. Transfected cells can be selected for the presence of the heavy chain plasmid with HAT and for the light chain plasmid with G418.

Two new restriction enzyme sites were engineered in both expression plasmids, a 5' site in the L-V intron, and a 3' site in the J3'-flanking sequences. Since these mutations were made in non-coding sequences, nucleotide changes are neutral and will not affect the reading frame. The correct reading frame is maintained in splicing the mouse leader to the chicken V domain at nucleotide −4, and in splicing the chicken J to the mouse C domains. Splice signals are conserved between the mouse and the chicken, and were not altered by the insertion of these new sites.

For the new heavy chain expression vector, $pEV_HC_{\gamma l}$-SN, the 5' site was made by mutating the nucleotides at 12–17 in the mouse L-V intron by two-step PCR to encode a Spe I site. The 3' site was engineered by cloning an oligonucleotide linker that created a Not I site into the BamHI site 197 nucleotides from the J boundary (FIG. 1A). For the new light chain expression vector, $\lambda_2\Delta_2$ke-CX, the 5' site was made by cloning an oligonucleotide linker that created a new Cla I site into the Pst I site at nucleotide 18 in the L-V intron in $\lambda_2\Delta_2$ke. The 3' site was made by inserting an oligonucleotide linker creating a new Xho I site into the Hind III site 13 n. from the J boundary (FIG. 1).

PCR primer design. Because there is a single expressed locus for the heavy chain and the light chain in chickens, a single PCR primer pair was used to amplify the expressed heavy chain and light chain antigen binding exons from genomic DNA. The PCR primers are designed to hybridize in the L-V intron and the J 3'-flanking sequences of the chicken heavy chain and light chain immunoglobulin gene, at positions comparable to the restriction enzyme sites created in the expression vectors. These primers will amplify the complete antigen binding domain and some of the adjacent flanking sequences. In addition, each includes the appropriate new restriction enzyme site at its 5' end so the product amplified by PCR can be directly cloned into the expression vector. For the chicken heavy chain (Reynaud et al., 1989), the 5' primer, HCSpe, hybridizes at n. 112–131 in the chicken heavy chain L-V intron and includes a Spe I site; the 3' primer, HCNot, hybridizes 17 n. 3' of the J boundary, and includes a Not I site. These primers amplify from genomic DNA a product of about 530 base pairs that include the remaining 83 n. of chicken L-V intron, the rearranged VDJ gene segment, and 35 noncoding nucleotides adjacent to the J boundary. For the chicken light chain, the primers LV and 839 (McCormack et al., 1989) were modified by the addition of restriction sites: Cla I was added to LV and Xho I to 839 to make the primers LVCla and 839Xho respectively. The product amplified by PCR from genomic DNA is approximately 500 base pairs that include the remaining 103 n. of the chicken L-V intron, the rearranged VJ gene segment and 33 noncoding nucleotides adjacent to the J boundary.

Chicken immunization, fusion and screening. An adult female chicken was immunized with a peptide-carrier complex containing the 13 amino acid sequence found in the carboxy-terminus of the human cystic fibrosis transmembrane conductance regulator (CFRT) protein. The animal was injected with approximately 400 micrograms of the peptide-carrier (CFTR-KLH) complex emulsified in complete Freund's adjuvant administered subcutaneously over the ribcage. Twelve days after the first immunization, the chicken was given an intravenous boost of 100 micrograms of antigen in saline. On day thirteen, the animal was sacrificed by carbon dioxide inhalation and the spleen extracted for lymphocyte preparation.

Lymphocytes were extracted from the spleen, and separated from red blood cells. The cells were fused with the chicken B-cell line R27H4 (Nishinaka et al., 1989, 1991) using standard cell fusion methodology. The fusion was plated in 24 well plates, and selected in medium containing HAT. 100% of the wells demonstrated growth. Supernates from positive wells were screened for the presence of CFTR-specific antibodies by ELISA. Out of 360 supernatants, 21 exhibited CFTR-specificity.

Cloning the chicken anti-CFTR heavy and light chain variable domains. Genomic DNA was made from four chicken B-cell/R27H4 hybridomas and used as the template in polymerase chain reactions to amplify the specific anti-CFTR antibody heavy and light chain variable domain produced by each cell line. These PCR products were cloned into the expression vectors and sequenced; the amino acid sequence of the variable domains of each heavy chain and light chain was derived from the DNA sequence. In addition, genomic DNA, made from chicken bursal B-cells at embryonic day 17 (Thompson et al., 1987), was used as the template to amplify at random heavy and light chain variable domains. These PCR products were used to make antibodies of unknown specificity that served as controls.

TABLE 3

Amino acid sequence of heavy Chain and light chain variable domain
(light chain germline = SEQ
ID NO:11; anti-CFTR 4-9 = SEQ ID NO:12 anti-CFTR 15-16 = SEQ ID NO:13;
unknown 2 = SEQ
ID NO:14; Heavy chain germline = SEQ ID NO:15; anti-CFTR 4-9 = SEQ ID
NO:16 anti CFTR
15-16 = SEQ ID NO:17; unknown 8 = SEQ ID NO:18)

|  | 1 | 50 |
|---|---|---|
| germline | MAWTSLILSLLALCSGSLVQAALTQPSSVSANPGGTVKITCSGDSSYYGW | |
| anti-CFTR 4-9 | MAWTSLILSLLALCSGSLVQAALTQPSSVSANPGETVKITCSGGSMMYGW | |
| anti-CFTR 15-16 | MAWTSLILSLLALCSGSLVEAELIQPTSVSANPGETVKITCSGDTIYIGW | |
| unknown 2 | MAWTSLILSLLALCSGSLVQAALTQPASVSANPGETVEITCSGDSSYYGW | |
|  | 51 | 100 |
| germline | YQQKAPGSAPVTVIYDNTNRPSNIPSRFSGSKSGSTATLTITGVRADDNA | |
| anti-CFTR 4-9 | YQQKAPGSAPVTLIYYNSQRPSDIPSRFSGSLSGSTNTLTITGVQVEDEA | |
| anti-CFTR 15-16 | YQQKAPGSAPVTVIYDNTTRPSNIPSRFSGSLSGSTNTLTITGVQVEDEA | |
| unknown 2 | YQQKAPGSAPVTLIYDNTNRPSNIPSRFSGSKSGSTATLTITGVRADDEG | |
|  | 101 | 126 |
| germline | VYYCASTDSSSTAXGIFGAGTTLTVL | |
| anti-CFTR 4-9 | VYFCGSWDNSAGYVGIFGAGTTLTVL | |
| anti-CFTR 15-16 | VYFCANADSSSTA.GIFGAGTTLTVL | |
| unknown 2 | IYYCASTDSSSTA..AFGAGTTLTVL | |

Heavy Chain

|  | mouse | chicken |
|---|---|---|
|  |  | CDR 1 |
| germline |  | MGWSCIMLFLAATATGLMAAVTLDESGGGLQTPGRALSLVCKASGFTFSS |

TABLE 3-continued

Amino acid sequence of heavy Chain and light chain variable domain
(light chain germline = SEQ
ID NO:11; anti-CFTR 4-9 = SEQ ID NO:12 anti-CFTR 15-16 = SEQ ID NO:13;
unknown 2 = SEQ
ID NO:14; Heavy chain germline = SEQ ID NO:15; anti-CFTR 4-9 = SEQ ID
NO:16 anti CFTR
15-16 = SEQ ID NO:17; unknown 8 = SEQ ID NO:18)

| | |
|---|---|
| anti-CFTR 4-9 | MGWSCIMLSLAATATGLMAAVTLDESGGGLQTPRGALSLVCKASGFTFSp |
| anti-CFTR 15-16 | MGWSCIMLSLAATATGLMAAVTLDESGGGLQTPGGGLSLVCKASGFTFSS |
| unknown 8 | MGWSCIMLFLAATATGLMAAVTLDESGGGLQTPGGALSLVCLGSGFDFSS |
| | CDR 2 |
| germline | YNMGWVRQAPGKGLEFVAGIDNTGRYTGYGSAVKGRATISRDNGQSTVRL |
| anti-CFTR 44-9 | YLMHWVRQAPGKGLEWVGGIRSDGSKTGYGAAVKGRATISRDNGQSTVRL |
| anti-CFTR 15-16 | NGMGWVRQAPGKGLEYVAGISSSGKYTGYGSAVKGRATISRDNGQSTVRL |
| unknown 8 | TDMGWVRQAPGKGLEFVAGIYSTPSGTGYAPAVRGRATISRDNGQSTLRL |
| | CDR 3 |
| germline | QLNNLRAEDTGTYYCAKAAGSAYGCGAYTA ...GSIDAWGHGTEVIVSS |
| anti-CFTR 4-9 | QLNNLRAEDTATYYCAKESGSGGSTGSSYA ...ANIDAWGHGTEVIVSS |
| anti-CFTR 15-16 | QLNNLRAEDTATYYCAKGGRSGFTCVI........ SXTWGHGTEVIVSS |
| unknown 8 | QLNNLRAEDTGTYYCAKAAGSGYCSSDATIA   GSIDAWGHGTEVIVSS |

Transfection and selection of stable cell lines. Transfectoma technology (Morrison et al., 1985) was used to express the chimeric chicken-mouse antibody genes encoded by the recombinant plasmids. Stable cell lines secreting properly assembled antibody molecules were made by cotransfecting a pair of the recombinant heavy chain (HC) and light chain (LC) expression vectors into the non-secreting mouse myeloma cell line P3x63.Ag8.653 at the molar ratio 7.5:1::HC:LC. Transfectants were grown in the presence of G418 which will select for the presence of the light chain vector only. By cotransfecting an excess of heavy chain plasmid, transfectants were obtained expressing both heavy and light chain molecules. Approximately 30% of the single-cell clones made from selected bulk transfectants were positive for specific antibody production by ELISA.

Screening and quantitation of antibodies. In order to screen the transfectants and to quantitate antibodies of unknown specificity, an ELISA protocol was designed to detect the mouse portions of the chimeric antibodies. Plates were coated with anti-mouse $IgG_1$ antibody. This will capture chimeric antibodies in tissue culture supernate that contain the mouse constant ($C_{\gamma l}$) domain. AKP-anti mouse $\lambda 1+2$ was then used to detect the captured antibody by binding to the mouse $\lambda 2$ light chain portion of the antibody. Tissue culture supernates from the hybridoma cell line 2D3.8 that secretes a wholly mouse $IgG_1\lambda_2$ antibody was used as a positive control, and purified mouse $IgG_1\lambda$ was used to generate the standard curve. The amount of antibody present in tissue culture medium of a mature ($4^+$ day culture) was estimated to be 0.6–1.2 mg/ml for 2D3.8, and 60–120 ng/ml for the transfected cell lines.

To screen and identify transfectomas secreting CFTR antibodies, an ELISA protocol was designed to capture antibodies specific for the immunizing peptide. The CFTR peptide conjugated to KLH and KLH alone had been used to identify positive clones of the original chicken B cell/R27H4 fusion. Now, clones of transfected cells were screened on plates coated with CFTR peptide-BSA conjugate and detected with AKP-anti-chicken IgY or AKP anti-mouse $\lambda 1+2$. Single cell clones secreting higher levels of antibody into the medium were expanded; so far, antibody production has been maintained at high levels for six months, as monitored by western blot and ELISA.

Purification and analysis of the chimeric antibodies. The heavy chain and light chain molecules, present in extracts of transfected cell cytoplasmic proteins and tissue culture supernates, were analyzed by western blot using reagents that would identify both the chicken and the mouse portions of the chimeric molecules. As shown in FIG. 2A, both heavy and light chains are synthesized in approximately equivalent amounts. In addition, proteins were purified from tissue culture supernates by chromatography on Protein A or Protein G, which binds the Fc receptor of the mouse immunoglobulin heavy chain constant domain. The proteins eluted from these columns were the heavy chain molecules that were specifically bound and retained on the column, and light chain molecules that would copurify only if in a complex with heavy chain molecules. Such a complex was present in column eluants and migrated in native gel electrophoresis at a rate consistent with its composition being $H_2L_2$, a properly assembled antibody molecule with a mass of approximately 180 kD. In denaturing gel electrophoresis, it is demonstrated that this complex contains both heavy chain and light chain molecules (FIG. 2B).

To confirm the puntative CFTR antibodies were specifically recognizing the CFTR peptide, a dilution series of purified CFTR1 and CFTR2 antibodies and three "unknown" antibodies were tested in an ELISA reaction designed to show that binding to the CFTR peptide was specific. Antibodies were tested for binding to the CFTR peptide and to the peptide CSD.2 which contains an epitope of the human IAP protein (Duckett et al., 1996). The two anti-CFTR-antibodies were specifically captured by the CFTR peptide and had a similar affinity for the peptide at the dilutions tested. The CFTR antibodies did not bind to the CSD.2 peptide; the unknown antibodies were captured by neither the CFTR nor the CSD.2 peptide (FIG. 3).

Detection of the full length CFTR protein. The CFTR antibodies 1 and 2, generated against the human CFTR carboxy-terminal peptide, were also used in experiments to detect the full length mouse CFTR protein. The CFTR carboxy-terminal thirteen amino acids are 92% identical between human (Riordan et al., 1989) and mouse (Tata et al., 1991). The single difference is the conservative replacement of the aspartic acid at position #10 in the human sequence with a glutamic acid in the mouse.

human KEETEEEVQDTRL (SEQ ID NO:19)
mouse KEETEEEVQETRL (SEQ ID NO:20)

Therefore, it was predicted that these antibodies could be used in an immunohistochemical assay to localize the full length mouse CFTR protein present in mouse lung. Dilutions of purified CFTR antibodies 1 and 2 were incubated with sections of mouse lung and detected with biotinylated anti-mouse antibody and HRP-avidin; AEC and $H_2O_2$ react to produce a red stain at the site of the antibody localization. As shown in FIG. 4, both antibodies specifically localize the CFTR protein to the single layer of nonciliated epithelial cells lining the terminal bronchioles and alveolae (Bunkitt et al., 1993). Background staining by the secondary biotinylated anti-mouse antibody identifies the blood vessels where natural occurring mouse antibodies are present. These same cells were shown to be positive for CFTR mRNA by in situ hybridization of antisense RNA probes (Whitsett et al., 1992). The chimeric CFTR1 and 2 antibodies differ in their affinity for the CFTR protein. A 1:500 dilution of CFTR1 is sufficient to stain the epithelial cell layer while a 1:50 dilution of CFTR2 is required to achieve comparable staining. The control chimeric antibody, 8:2, does not stain at any concentration tested.

XIII. References

The following references, to the extent that they provide exemplary procedural details or other information supplementary to that set forth herein, are incorporated by reference:

Abbondanzo et al., Breast Cancer Res. Treat., 16:182 (#151), 1990.

Alonso, A., Change, L. A., Murialdo, H., "Analysis of the expression of murine λ genes transfected into immunocompetent cell lines," Mol. Immun., 27:115–127, 1990.

Allred et al., Breast Cancer Res. Treat., 16:182(#149), 1990.

American Research Products, Inc., 1995 Product Catalogue.

Baba, T. W., Giroir, B. P., and Humphries, E. H., "Cell lines derived from avian lymphomas exhibit two distinct phenotypes," Virology, 144:139–151, 1985.

Baichwal and Sugden, In: Kucherlapati R. ed. Gene transfer. New York: Plelnum Press, pp. 117–148, 1986.

Bauwens, R. M., Kint, J. A., Devos, M. P., Van Brussel, K. A., De Leenheer, A. P., "Production, purification and characterization of antibodies to 1,25-dihydroxyvitamin D raised in chicken egg yolk," Clin. Chim. Acta, 170:37–44, 1987.

Benvenisty and Neshif, Proc. Nat. Acad. Sci. USA, 83:9551–9555, 1986.

Borrebaeck, C. A. K., ed. Antibody Engineering, second edition, Oxford University Press 1995

Bothwell, A. L. M., Paskind, M., Reth, M., Imanishi-Kari, T., Rajewsky, K., Baltimore, D., "Heavy chain variable region contribute to the $Np^b$ family of antibodies: somatic mutation evident in a γ2a variable region," Cell, 24:625–637, 1981.

Brown et al., Breast Cancer Res. Treat., 16: 192(#191), 1990.

Burger, D., Ramus, M-A., Schapira, M., "Antibodies to human plasma kallikrein from egg yolks of an immunized hen: preparation and characterization," Thrombosis Res., 40:283–288, 1985.

Burkitt, H. G., Young B., Heath J. W., eds., Wheater'sFunctional Histology, third edition, Churchill Livingstone (Medical Division of Longman Group UK Limited), 1993.

Carroll, S. B., Stollar, B. D., "Antibodies to calf thymus RNA polymerase 11 from egg yolks of immunized hens," J. Biol. Chem., 258:24–26, 1983.

Chen and Okayama, Mol. Cell Biol., 7:2745–2752, 1987.

Cheng, S. H., Gregory, R. J., Marshall, J., Paul, S., Souza, D. W., White, G. A., O'Riordan, C. R., and Smith, A. E., "Defective intracellular transport and processing of CFTR is the molecular basis of most cystic fibrosis," Cell, 63:827–834, 1990.

Cinader, B., "Specificity and inheritance of antibody response: a possible steering mechanism," Nature, 188:619–622, 1960.

Coffin, In: Virology, Fields et al. (eds.), New York: Raven Press, pp. 1437–1500, 1990.

Coloma, M. J., Hastings, A., Wims, L. A., Morrison, S. L., "Novel vectors for the expression of antibody molecules using variable regions generated by polymerase chain reaction," J. Immun. Meth., 152:89–104, 1992.

Coupar et al., Gene, 68:1–10, 1988.

Denning, G. M., Ostedgaard, L. S., Cheng, S. H., Smith A. E., and Welsh, M. J., "Localization of cystic fibrosis transmembrane conductance regulator in chloride secretory epithelia," J. Clin. Invest., 89:339–349, 1992.

Diamond, G., Scanlin, T. F., Zasloff, M. A., Bevins, C. L., "A cross-species analysis of the cyctic fibrosis transmembrane conductance regulator," J. Biol. Chem., 266:22761–22769, 1991.

Drumm, M. L., Collins, F. S., "Molecular biology of cystic fibrosis," Mol. Gen. Med., 3:33–68, 1993.

Dubensky et al., "Direct transfection of viral and plasmid DNA into the liver or spleen of mice," Proc. Nat. Acad. Sci. USA, 81:7529–7533, 1984.

Duckett, C. S., Nava, V. E., Gedrich, R. W., Clem, R. J., VanDongen J. L., Gilfillan, M. C., Shields, H., Hardwick, J. M., Thompson, C. B., "A conserved family of cellular genes related to the baculovirus iap gene and encoding apoptosis inhibitors," EMBO J., 15:2685–2694, 1996.

Fechheimer et al., "Transfection of mammalian cells with plasmid DNA by scrape loading and sonication loading," Proc. Natl. Acad. Sci. USA, 84:8463–8467, 1987.

Ferkol et al., FASEB J, 7:1081–1091, 1993.

Fertel, R., Yetiv, J. Z., Coleman, M. A., Schwarz, R. D., Greenwald, J. E., Bianchine, J. R., "Formation of antibodies to prostaglandins in the yolk of chicken eggs," Biochem. Biophys. Res. Comm., 102:1028–1033, 1981.

Fraley et al., "Entrapment of a bacterial plasmid in phospholipid vesicles: Potential for gene transfer," Proc. Natl. Acad. Sci USA, 76:3348–3352, 1979.

Freshner, R. I. *"Animal Cell Culture: a Practical Approach"*, Second Edition, Oxford/New York, IRL Press, Oxford University Press, 1992.

Fuller, C. M., Howarw, M. B., Bedwell, D. M., Frizzel, R. A., Benos, D. J., "Antibodies against the cystic fibrosis transmembrane regulator," *Am. J. Physiol.,* 262 (Cell Physiol. 31):C396–C404, 1992.

Gassmann, M., Thommes, P., Weiser, T., Hubscher, U., "Efficient production of chicken egg yolk antibodies against a conserved mammalian protein," *The FASEB J.,* 4:2528–2532, 1990.

Gefter et al., *Somatic Cell Genet.,* 3:231–236, 1977.

Ghosh and Bachhawat, "Targeting of liposomes to hepatocytes," In: Wu G, Wu C ed. Liver diseases, targeted diagnosis and therapy using specific receptors and ligands. New York: Marcel Dekker, pp. 87–104, 1991.

Gillies, S. D., Tonegawa, S., "Expression of cloned immunoglobulin genes introduced into mouse L cells," *Nuc. Acids. Res.,* 11:7981–7997, 1983.

Gingeras et al., PCT Application WO 88/10315.

Goding, 1986, In: *Monoclonal Antibodies: Principles and Practice,* 2d ed., Orlando, Fla., Academic Press, 1986, pp. 60–61, and 71–74.

Gopal, *Mol. Cell Biol.,* 5:1188–1190, 1985.

Graham, F. L. & Van Der Eb, A. J. *Virology* 52:456–467, 1973.

Graham, F. & Prevec, L. In: *Methods in Molecular Biology: Gene Transfer and Expression Protocols* 7. Murray, E. J. Editors. Clifton, N.J.: Humana Press, 109–128 and 205–225, 1991.

Gregory, R. J., Cheng, S. H., Rich, D. P., Marshall, J., Paul, S., Hehir K., Ostedgaard, L., Klinger, K. W., Welsh, M. J., and Smith, A. E., "Expression and characterization of the cystic fibrosis transmembrane conductance regulator," *Nature,* 347:382–386, 1990.

Grunhaus and Horwitz, *Seminar in Virology,* 3:237–252, 1992.

Hadge, D., Ambrosius, H., "Evolution of low molecular weight immunoglobulins-IV. IgY-like immunoglobulins of birds, reptiles and amphibians, precursors of mammalian IgA," *Mol. Immunol.,* 21:699–707.

Harland and Weintraub, *J. Cell Biol.,* 101:1094–1099, 1985.

Heinrichs A., Milstein, C., Gherardi, E., "Universal cloning and direct sequencing of rearranged antibody V genes using C region primers, biotin-captured cDNA and one-side PCR," *J. Immun. Meth.,* 178:241–251, 1995.

Hermonat and Muzycska, *Proc. Nat. Acad. Sci. USA,* 81:6466–6470, 1984.

Honjo, T., Obata, M., Yamawaki-Kataoka, Y., Kataoka, T., Kawakami, T., Takahashi, N., Mano, Y., "Cloning and complete nucleotide sequence of mouse immunoglobulin γ1 chain gene," *Cell,* 18:559–568, 1979.

Horton, J. J., Holden, C. A., Ward, P. J., MacDonald D. M., Sanderson, A. R., "Exploitation of phylogenetic distance in cell surface immune labeling:Studies with $beta_2$-microglobulin," *J. Invest. Derm.,* 85:96–99, 1984.

Horwich et al., *J. Virol.,* 64P:642–650, 1990.

Huston, J. S., Levinson, D., Mudgett-Hunter, M., Tai, M-S., Novotny, J., Margolies, M. N., Ridge, R. J., Bruccoleri, R. E., Haber, E., Crea, R., Oppermann, H., "Protein engineering of antibody binding sites: recovery of specific activity in an anti-digoxin single-chain Fv analogue produced in Escherichia coli, " *Proc. Nat. Acad. Sci. USA,* 85:5879–5883, 1988.

Innis et al., *PCR Protocols,* Academic Press, Inc., San Diego Calif., 1990.

Kato et al, *J. Biol. Chem.,* 266:3361–3364, 1991.

Klein et al., *Nature,* 327:70–73, 1987.

Kohler, G., Milstein, C., "Continuous cultures of fused cells secreting antibody of predefined specificity," *Nature,* 256:495–497, 1974.

Kohler and Milstein, *Nature,* 256:495–497, 1975.

Kohler and Milstein, *Eur. J. Immunol.,* 6:511–519, 1976.

Kwoh et al., *Proc. Nat. Acad. Sci. USA,* 86:1173, 1989.

Larrick, J. W., Danielsson, L., Brenner, C. A., Abrahamson, M., Fry, K. E., Borrebaeck, C. A. K., "Rapid cloning of rearranged immunoglobulin genes from human hybridoma cells using mixed primers and the polymerase chain reaction," *Biochem. Biophys. Res. Comm.,* 160:1250–1256, 1989.

Larsson, A., Balow, R-M., Lindahl, T. L., Forsberg, P-O., "Chicken antibodies: taking advantage of evolution-a review," *Poultry Sci.,* 72:1807–1812, 1993.

Lee, K., Ametani, A., Schimizu, M., Hatta, H., Yamamoto, T., Kaminogawa, S., "Production and characterization of anti-human insulin antibodies in the hen's egg," *Agric. Biol. Chem.,* 55:2141–2143, 1991.

McCafferty, J., Griffiths, A. D., Winter, G., Chiswell, D. J., "Phage antibodies: filamentous phage displaying antibody variable domains," *Nature,* 348:552–554, 1990.

McCormack, W. T., Hurley, E. A., Thompson, C. B., "Germ line maintenance of the pseudogene donor pool for somatic gene conversion in chickens," *Mol. Cell. Biol.,* 13:8211–830, 1993.

McCormack, W. T., Tjoelker, L. W., Carlson, L. M., Petryniak, B., Barth, C. F., Humphries, E. H., Thompson, C. B., "Chicken $Ig_L$ gene rearrangement involves deletion of a circular episome and addition of single nonrandom nucleotides to both coding segments," *Cell,* 56:785–791, 1989.

McCormack, W. T., Tjoelker, L. W., Thompson, C. B., "Avian B-cell development: generation of an immunoglobulin repertoire by gene conversion," *Annu. Rev. Immunol.,* 9:219–241, 1991.

Macejak and Sarnow, *Nature,* 353:90–94, 1991.

Morrison, S. L., "Transfectomas provide novel chimeric antibodies," *Science,* 229:1202–1207, 1985.

Morrison, S. L., "Transfer and expression of immunoglobulin genes," *Ann. Rev. Immunol.,* 2:239–256, 1984.

Morrison, S. L., Coloma, M. J., Espinoza, D., Hastings, A., Shin, S-U., Wims, L. A., and Wright, A., "Vectors and approaches for the eukaryotic expression of antibodies and antibody fusion proteins," in Antibody Engineering, 2nd edition, (Borrebaeck, C. A. K. ed.) (see reference to book under Borrebaeck) Chapter 9 pp267–294.

Morrison, S. L., Johnson, M. J., Herzenberg, L. A., Oi, V. T., "Chimeric human antibody molecules: mouse antigen-binding domains with human constant region domains," *Proc. Natl. Acad. Sci., USA,* 81:6851–6855, 1984.

Nakamura et al., In: *Handbook of Experimental Immunology* (4th Ed.), Weir, E., Herzenberg, L. A., Blackwell, C., Herzenberg, L. (eds). Vol. 1, Chapter 27, Blackwell Scientific Publ., Oxford, 1987.

Neuberger, M. S., "Expression and regulation of immunoglobulin heavy chain gene transfected into lymphoid cells," *EMBO J.*, 8:1373–1378, 1983.

Nicolas and Rubenstein, "Retroviral vectors," In: *Vectors: A survey of molecular cloning vectors and their uses*, Rodriquez & Denhardt (eds.), Stoneham: Butterworth, pp. 493–513, 1988.

Nicolau and Sene, *Biochim. Biophys, Acta*, 721:185–190, 1982.

Nicolau et al., *Methods Enzymol.*, 149:157–176, 1987.

Nishinaka, S., Matsuda, H., Murata, M., "Establishment of a chicken x chicken hybridoma secreting specific antibody," *Int. Arch. Allergy Immunol.*, 89:416–419, 1989.

Nishinaka, S., Suzuki, T., Matsuda, H., Murata, M., "A new cell line for the production of chicken monoclonal antibody by hybridoma technology," *J. Immun. Meth.*, 139:217–222, 1991.

Ohara et al., *Proc. Natl. Acad. Sci. USA*, 86:5673–5677, 1989.

Orlandi, R., Gussow, D. H., Jones, P. T., Winter, G., "Cloning immunoglobulin variable domains for expression by the polymerase chain reaction," *Proc. Natl. Acad. Sci. USA*, 86:3833–3837, 1989.

Parvari, R., Avivi, A., Lentner, F., Ziv, E., Tel-Or, S., Burstein, Y., Schechter, I., "Chicken immunoglobulin γ-heavy chains: limited VH gene repetoire, combinational diversification by D gene segments and evolution of the heavy chain locus," *EMBO J.*, 7:739–744, 1988.

Parvari, R., Etty, Z., Lentner, F., Shoshana, T-O., Burstein, Y., and Schechter, I., "Analysis of chicken immunoglobulin light chain cDNA clones indicate a few germline Vγ genes and allotypes of the Cγ locus," *EMBO J.* 6:97–103, 1987.

Pelletier and Sonenberg, *Nature*, 334:320–325, 1988.

Perales et al., *Proc. Natl. Acad. Sci. USA*, 91:4086–4090, 1994.

Potter et al., *Proc. Nat. Acad. Sci. USA*, 81:7161–7165, 1984.

Renan, *Radiother. Oncol.*, 19:197–218, 1990.

Reynaud, C.-A., Anquez, V., Dahan, A., Weill, J.-C., "A single rearrangement event generates most of the chicken immunoglobulin light chain diversity," *Cell*, 40:283–291, 1985.

Reynaud, C.-A., Anquez, V., Grimal, H., Weill, J.-C., "Somatic hypoconversion diversifies the single $V_H$ gene of the chicken with a high incidence in the D region," *Cell*, 59:171–183, 1989.

Reynaud, C.-A., Dahan, A., Weill, J.-C., "Complete sequence of a chicken lambda light chain immunoglobulin derived from the nucleotide sequence of its rnRNA," *Proc. Natl. Acad. Sci. USA*, 80:4099–4103, 1983.

Rich, D. P., Anderson, M. P., Gregory, R. J., Cheng, S. H., Paul, S., Jefferson, D. M., McCann, J. D., Klinger, K. W., Smith, A. E., and Welsh, M. J., "Expression of cystic fibrosis transmembrane conductance regulator corrects defective chloride channel regulation in cystic fibrosis airway epithelial cells," *Nature*, 347:358–363, 1990.

Ridgeway, In: Rodriquez R L, Denhardt D T, ed. *Vectors: A survev of molecular cloning vectors and their uses.* Stoneham: Butterworth, pp. 467492, 1988.

Riordan, J. R., Rommens, J. M., Kerem, B., Alon, N., Rozmahel, R., Grzelczak, Z., Zielenski, J., Lok, S., Plavsic, N., Chou, J-L., Drumm, M. L., lannuzzi, M. C., Collins, F. S., Tsui, L-C., "Identification of the cystic fibrosis gene: cloning and characterization of complementary DNA," *Science*, 245:1066–1072, 1989.

Rippe et al., *Mol. Cell Biol.*, 10:689–695, 1990.

Roux et al., *Proc. Natl. Acad. Sci. USA*, 86:9079–9083, 1989.

Sambrook, et a., *Molecular cloning: a laboratory manual.* 2nd. New York: Cold Spring Harbor Laboratory Press, 1989.

Schuh, T. J., Ahrens, H., Mogensen, M. D., Gorski, J., and Mueller, G. C., "Polyclonal antibodies from rabbits and chickens against the estrogen receptor and related peptides," *Receptor*, 2:93–107, 1992.

Sharon, J., Gefter, M. L., Manser, T., Morrison, S. L., Ptashne, M., "Expression of a $V_HC_k$ chimeric protein in mouse myeloma cells," *Nature*, 309:364–367, 1984.

Simon, T., Rajewsky, K., "'Enhancer-constitutive' vectors for the expression of recombinant antibodies," *Nuc. Acids. Res.*, 16:354, 1988.

Song, C-S., Yu, J-H., Bai, D. H., Hester, P. Y., Kim, K-H., "Antibodies to the α-subunit of insulin receptor from eggs of immunized hens," *J. Immunol.*, 135:3354–3359, 1985.

Tata, F., Stanier, P., Wicking, C., Halford, S., Kruyer, H., Lench, N. J., Scambler, P. J., Hansen, C., Braman, J. C., Williamson, R., Wainwright, B. J., "Cloning the mouse homolog of the human cystic fibrosis transmembrane conductance regulator gene," *Genomics*, 10:301–307, 1991.

Temin, "Retrovirus vectors for gene transfer: Efficient integration into and expression of exogenous DNA in vertebrate cell genome," In: *Gene Transfer*, Kucherlapati (ed.), New York: Plenum Press, pp. 149–188, 1986.

Thompson, C. B., Neiman, P. E., "Somatic diversification of the chicken immunoglobulin light chain is limited to the rearranged variable gene segment," *Cell*, 48:369–378, 1987.

Tur-Kaspa et al., *Mol. Cell Biol.*, 6:716–718, 1986.

Wagner et al., *Proc. Natl. Acad. Sci.* 87(9):3410–3414, 1990.

Walker et al., *Proc. Natl. Acad. Sci. USA*, 89:392–396, 1992.

Weill, J.-C., Reynaud, C.-A., Lassila, O., Pink, J. R. L., "Rearrangement of chicken immunoglobulin genes is not an ongoing process in the embryonic bursa of fabricius," *Proc. natl. Qacad. Sci. USA*, 83:3336–3340, 1986.

Whitsett, J. A., Dey, C. R., Stripp, B. R., Wikenheiser, K. A., Clark, J. C., Wert, S. E., Gregory, R. J., Smith, A. E., Cohn, J. A., Wilson, J. M., Engelhardt, J., "Human cystic fibrosis transmembrane conductance regulator directed to respiratory epithelial cells of transgenic mice," *Nat. Genetics*, 2:13–20, 1992.

Winter, G., Milstein, C., "Man-made antibodies," *Nature*, 349:293–299, 1991.

WO 90/07641 filed Dec. 21, 1990.

Wong et al., "Appearance of β-lactamase activity in animal cells upon liposome mediated gene transfer," *Gene*, 10:87–94, 1980.

Woolley, J. A., Landon, J., "Comparison of antibody production to human interleukin-6 (IL-6) by sheep and chickens," *J. Immun. Meth.*, 178:253–265, 1995.

Wu, G. E., Govindji, N., Hozumi, N., Murialdo, H., "Nucleotide sequence of a chromosomal rearranged λ2 immunoglobulin gene of mouse," *Nuc. Acids. Res.*, 10:3831–3843, 1982.

Wu and Wu, J. "Receptor-mediated in vitro gene transfections by a soluble DNA carrier system," *Biol. Chem.*, 262:4429–4432, 1987.

Wu and Wu, "Evidence for targeted gene delivery to HepG2 hepatoma cells in vitro," *Biochemistry,* 27:887–892, 1988.

Wu et al., *Genomics,* 4:560, 1989.

Wu and Wu, *Adv. Drug Delivery Rev.,* 12:159–167, 1993.

Yamanaka, H. I., Inoue, T., Ikeda-Tanaka, O., "Chicken monoclonal antibody isolated by a phage display system," *J. Immun.,* 157:1156–1162, 1996.

Yang et al., "In vivo and in vitro gene transfer to mammalian somatic cells by particle bombardment," *Proc. Natl. Acad. Sci USA,* 87:9568–9572, 1990.

Zelin et al., "High-velocity mechanical DNA transfer of the chloramphenicol acetyltransferase gene into rodent liver, kidney and mammary gland cells in organ explants and in vivo," *FEBS Lett.,* 280:94–96, 1991.

---

What is claimed is:

1. A method for generating monoclonal antibodies comprising the steps of:
   (i) immunizing a chicken with an antigen composition;
   (ii) isolating B cells from said chicken;
   (iii) immortalizing said B cells;
   (iv) selecting an immortalized antibody producing B cell and preparing nucleic acids encoding the antigen binding exons of the light and heavy chain genes thereof;
   (v) cloning said heavy and light chain antigen binding regions, respectively, into vectors encoding
     (a) non-chicken constant and leader regions of an immunoglobulin heavy chain,
     (b) non-chicken constant and leader regions of an immunoglobulin light chain;
   (vi) transferring said vectors into a suitable host cell;
   (vii) culturing said host cell; and
   (viii) isolating antibodies produced by said cell.

2. The method of claim 1, wherein said immortalizing comprises fusing said B cells to a chicken lymphoblastoid cell line.

3. The method of claim 1, wherein said immortalizing comprises infection of said B cells with an avian retrovirus.

4. The method of claim 1, wherein said preparing comprises isolating nucleic acids from the B cell of step (iv) and conducting PCR amplification of the coding sequences for said heavy and light chain antigen binding regions.

5. The method of claim 4, wherein said isolated nucleic acids comprise genomic DNA.

6. The method of claim 4, wherein the heavy chain PCR primers have the sequence of SEQ ID NO:7 and SEQ ID NO:8.

7. The method of claim 4, wherein the light chain PCR primers have the sequence of SEQ ID NO:9 and SEQ ID NO: 10.

8. The method of claim 1, wherein said antigen composition of step (i) comprises
   (a) an antigen selected from the group consisting of CFTR, transforming growth factor beta; transcription factors, DNA binding molecules; cyclin dependent kinases and RNA binding proteins; and
   (b) a pharmaceutical buffer carrier or diluent.

9. The method of claim 1, wherein said antigen composition of step (i) comprises
   (a) an antigen selected from the group consisting of lipids; phospholipids, and carbohydrates; and
   (b) a pharmaceutical buffer carrier or diluent.

10. The method of claim 1, wherein said selecting comprises screening the B cells of step (iii) for production of an antibody that binds to said antigen.

11. The method of claim 10, wherein said screening comprises measuring the binding of said antibodies to a target antigen.

12. The method of claim 11, wherein said measuring is performed by a method selected from the group consisting of ELISA, Western blot and immune precipitation.

13. The method of claim 1, wherein said host cell is a murine myeloma line.

14. The method of claim 1, wherein said culturing is performed in vitro.

15. The method of claim 1, wherein said culturing is performed in vivo.

16. The method of claim 15, wherein said in vivo culturing is performed in a mouse.

17. The method of claim 1, wherein said isolating comprises either or both of protein A affinity and ammonium sulfate precipitation.

* * * * *

UNITED STATES PATENT AND TRADEMARK OFFICE
CERTIFICATE OF CORRECTION

PATENT NO. : 6,316,600 B1
DATED : November 13, 2001
INVENTOR(S) : Nancy M. Michael, Mary Ann V. Accavitti and Craig B. Thompson It is certified that error appears in the above-identified patent and that said Letters Patent is hereby corrected as shown below:

<u>Title page, Item [54] and Column 1, line 2,</u>
Please delete "MONOCLONIAL" and insert -- MONOCLONAL -- therefor.

<u>Column 66,</u>
Lines 58, 60 and 61, please delete "in vivo" and insert -- *in vivo* -- therefor.

Signed and Sealed this

Second Day of July, 2002

Attest:

JAMES E. ROGAN
Attesting Officer    Director of the United States Patent and Trademark Office